(12) United States Patent
Holliger et al.

(10) Patent No.: US 9,228,179 B2
(45) Date of Patent: Jan. 5, 2016

(54) POLYMERASE

(71) Applicant: MEDICAL RESEARCH COUNCIL, Swindon (GB)

(72) Inventors: Philipp Holliger, Cambridge (GB); Marc D'Abbadie, London (GB); Claudia Baar, Cambridge (GB)

(73) Assignee: MEDICAL RESEARCH COUNCIL, Swindon (GB)

( * ) Notice: Subject to any disclaimer, the term of this patent is extended or adjusted under 35 U.S.C. 154(b) by 0 days.

(21) Appl. No.: 13/769,655

(22) Filed: Feb. 18, 2013

(65) Prior Publication Data

US 2013/0149749 A1    Jun. 13, 2013

Related U.S. Application Data

(63) Continuation of application No. 12/446,746, filed as application No. PCT/GB2007/004031 on Oct. 23, 2007, now abandoned.

(30) Foreign Application Priority Data

Oct. 23, 2006 (GB) .................................. 0621094.2
Nov. 30, 2006 (GB) .................................. 0623977.6

(51) Int. Cl.
   *C12N 9/12*    (2006.01)
(52) U.S. Cl.
   CPC ............ *C12N 9/1241* (2013.01); *C12N 9/1252* (2013.01)
(58) Field of Classification Search
   None
   See application file for complete search history.

(56) References Cited

U.S. PATENT DOCUMENTS

| 5,474,920 A | 12/1995 | Moses |
| 5,985,557 A | 11/1999 | Prudent et al. |
| 7,514,210 B2 | 4/2009 | Holliger et al. |
| 8,435,775 B2 | 5/2013 | Holliger et al. |
| 2002/0127623 A1 | 9/2002 | Minshull et al. |
| 2004/0005594 A1 | 1/2004 | Holliger et al. |
| 2004/0161767 A1 | 8/2004 | Baldwin et al. |

FOREIGN PATENT DOCUMENTS

| WO | WO-95/14782 A2 | 6/1995 |
| WO | WO-00/29428 A2 | 5/2000 |
| WO | WO-02/22869 A2 | 3/2002 |
| WO | WO-2005/024010 A1 | 3/2005 |
| WO | WO-2005/045015 A2 | 5/2005 |
| WO | WO-2008/029085 A2 | 3/2008 |
| WO | WO-2008/034110 A2 | 3/2008 |
| WO | WO-2008/050104 A1 | 5/2008 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Amblar et al. J. Biotechnol., 63(1): 17-27 (1998).*
Darby-Hughes et al., Detailed characterization of conditions for alignment of single-stranded and double-stranded DNA fragments on surfaces. *Biomedical Microdevices*. 5(1): 69-74 (2003).
Evans et al., Improving dideoxynucleotide-triphosphate utilisation by the hyper-thermophilic DNA polymerase from the archaeon *Pyrococcus furiosus*. *Nucl. Acids Res*. 28(5):1059-66 (2000).
Foldes-Papp et al., Fluorescently labeled model DNA sequences for exonucleolytic sequencing. *J. Biotech*. 86(3):203-24 (2001).
Franke-Whittle et al., Comparison of different labeling methods for the production of labeled target DNA microarray hybridization. *J. Microbiol. Meth*. 65(1): 117-26 (2006).
Ghadessy et al., Directed evolution of polymerase function by compartmentalized self-replication. *Proc. Natl. Acad. Sci. USA*. 98(8): 4552-7 (2001).
Ravenschlag, et al., "The use of MasterTaq Kit for PCR with humic material-contaminated DNA," eppendorf, 2 pages. (2000).
Ghadessy et al., Generic expansion of the substrate spectrum of a DNA polymerase by direction evolution. Nature Biotech. 22(6): 755-9 (2004).
Ravenschlag et al., The use of MasterTaq Kit for PCR with humic material-contaminated DNA. Applications No. 20 <<http://www.eppendorf.de/int/index.php?1=2&action=document&sitemap=1&docnode=26726&pb=e4f62a797b085396>>, May 2000.
Tasara et al., Incorporation of reporter molecule-labeled nucleotides by DNA polymerase. II. High-density labeling of natural DNA. *Nucl. Acids Res*. 31(10): 2636-46 (2003).
International Search Report and Written Opinion of the International Searching Authority, European Patent Office, PCT/GB2007/004031, dated Feb. 11, 2008.
International Preliminary Report on Patentability, PCT/GB2007/004031, dated May 7, 2009.
Amblar et al., Purification and properties of the 5'-3' exonuclease D10A mutant of DNA polymerase I from *Streptococcus pneumoniae*: A new tool for DNA sequencing. *J. Biotechnol.*, 63(1):17-27 (1998).

\* cited by examiner

*Primary Examiner* — Richard Hutson
(74) *Attorney, Agent, or Firm* — Marshall, Gerstein & Borun LLP

(57) ABSTRACT

An engineered DNA polymerase characterised in that the polymerase exhibits an enhanced ability to process nucleic acid in the presence of environmental and biological inhibitors compared to wild type DNA polymerase.

3 Claims, No Drawings

SEQUENCE LISTING

<160> NUMBER OF SEQ ID NOS: 18

<210> SEQ ID NO 1
<211> LENGTH: 2502
<212> TYPE: DNA
<213> ORGANISM: Artificial
<220> FEATURE:
<223> OTHER INFORMATION: Synthetic Polymerase

<400> SEQUENCE: 1

```
atggcgatgc ttcccctctt tgagcccaaa ggccgggtcc tcctggtgga cggccaccac       60
ctggcctacc gcaccttctt cgccctgaag ggcctcacca cgagccgggg cgaaccggtg      120
```

```
caggcggtct acggtttcgc caagagcctc ctcaaggccc tgaaggagga cgggtacaag    180
gccgtcttcg tggtctttga cgccaaggcc ccctccttcc gccacgaggc ctacgaggcc    240
tacaaggcgg ggagggcccc gacccccgag gacctccccc ggcagctcgc cctcatcaag    300
gagctggtgg acctcctggg gtttacccgc ctcgaggtcc aaggctacga ggcggacgac    360
gtcctcgcca ccctggccaa gaaggcggaa aaagaagggt acgaggtgcg catcctcacc    420
gccgaccggg acctctacca gctcgtctcc gaccgcgtcg ccgtcctcca ccccgagggc    480
cacctcatca ccccggagtg gctttgggag aagtacggcc tcaggccgga gcagtgggtg    540
gacttccgcg ccctcgtggg ggaccccctcc gacaacctcc ccggggtcaa gggcatcggg    600
gagaagaccg ccctcaagct cctcaaggag tggggaagcc tggaaaatct cctcaagaac    660
ctggatcggt aaagccgga aaacgtccgg gagaagatca aggcccacct ggaagacctc    720
aggctctcct ggagctctc ccgggtgcgt accgacctcc cctggaggt ggacctcgcc    780 caggggcggg agcccgaccg ggaagggctt agggccttcc tggagaggct ggagttcggc    840
agcctcctcc atgagttcgg ccttctggaa agccccaagg ccctggagga ggcccctgg    900 ccccaccgg aaggggcctt cgtgggcttt gtgctttccc gcaaggagcc catgtgggcc    960
gatcttctgg ccctggccgc cgccagggt ggtcgggtcc accgggcccc cgagccttat   1020
aaagccctca gggacttgaa ggaggcgcgg gggcttctcg ccaaagacct gagcgttctg   1080
gccctaaggg aaggccttgg cctcccgccc ggcgacgacc catgctcct cgcctacctc   1140 ctggacccctt ccaacaccac ccccgagggg gtggcccggc gctacggcgg ggagtggacg   1200
gaggaggcgc gggagcgggc cgcccttttcc gagaggctct tcgccaacct gtggggagg   1260 cttgaggggg aggagaggct cctttggctt taccggagg tggataggcc cctttccgct   1320
gtcctggccc acatggaggc cacaggggtg cgcctggacg tggcctatct cagggccttg   1380
tccctggagg tggccgagga gatcgcccgc ctcgaggccg aggtcttccg cctggccggc   1440 cacccccttca acctcaactc ccgggaccag ctggaaaggg tcctctttga cgagctaggg   1500
cttcccgcca tcggcaagac ggagaggacc ggcaagcgct ccaccagcgc cgccgtcctg   1560
gaggccctcc gcgaggccca ccccatcgtg gagaagatcc tgcagtaccg ggagctcacc   1620
aagctgaaga gcacctacat tgacccctttg ccggacctca tccacccag gacgggccgc   1680 ctccacaccc gcttcaacca gacggccacg gccacgggca ggctaagtag ctccgatccc   1740
aacctccaga acatccccgt ccgcaccccg cttgggcaga ggatccgccg ggccttcatc   1800
gccgaggagg ggtggctatt ggtggccctg gactatagcc agatagagct cagggtgctg   1860
gcccacctct ccggcgacga gaacctgatc cgggtcttcc aggaggggcg ggacatccac   1920
acggagaccg ccagctggat gttcggtgtc ccccgggagg ccgtggaccc cctgatgcgc   1980
cgggcggcca agacggtgaa cttcggcgtc ctctacggca tgtccgccca taggctctcc   2040
caggagcttt ccatcccta cgaggaggcg gtggcctta tagagcgcta cttccaaagc   2100
ttccccaagg tgcgggcctg gatagaaaag accctggagg agggagggaa gcggggctac   2160
gtggaaaccc tcttcggaag aaggcgctac gtgcccgacc tcaacgcccg ggtgaagagc   2220
gtcagggagg ccgcggagcg catggccttc aacatgccg tccagggcac cgccgccgac   2280
ctcatgaagc tcgccatggt gaagctcttc ccccgcctcc gggagatggg ggcccgcatg   2340
ctcctccagg tccacgacga gctcctcctg gaggcccccca agcgcgggc cgaggaggtg   2400 gcggctttgg ccaaggaggc catggagaag gcctatcccc tcgccgtacc cctggaggtg   2460
```

```
gaggtgggga tcggggagga ctggctttcc gccaagggtt ag                    2502
```

<210> SEQ ID NO 2
<211> LENGTH: 833
<212> TYPE: PRT
<213> ORGANISM: Artificial
<220> FEATURE:
<223> OTHER INFORMATION: Synthetic Polymerase

<400> SEQUENCE: 2

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Leu Pro Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
```

```
            355                 360                 365
Pro Pro Gly Asp Asp Pro Met Leu Leu Ala Tyr Leu Leu Asp Pro Ser
    370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Arg Leu Leu Trp Leu Tyr Arg
                420                 425                 430
Glu Val Asp Arg Pro Leu Ser Ala Val Leu Ala His Met Glu Ala Thr
        435                 440                 445
Gly Val Arg Leu Asp Val Ala Tyr Leu Arg Ala Leu Ser Leu Glu Val
    450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Arg Thr Gly Lys
                500                 505                 510
Arg Ser Thr Ser Ala Ala Val Leu Glu Ala Leu Arg Glu Ala His Pro
                515                 520                 525
Ile Val Glu Lys Ile Leu Gln Tyr Arg Glu Leu Thr Lys Leu Lys Ser
        530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Ile Ala Glu Glu Gly Trp Leu Leu Val
                595                 600                 605
Ala Leu Asp Tyr Ser Gln Ile Glu Leu Arg Val Leu Ala His Leu Ser
        610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Pro Glu Ala Val Asp
                645                 650                 655
Pro Leu Met Arg Arg Ala Ala Lys Thr Val Asn Phe Gly Val Leu Tyr
                660                 665                 670
Gly Met Ser Ala His Arg Leu Ser Gln Glu Leu Ser Ile Pro Tyr Glu
                675                 680                 685
Glu Ala Val Ala Phe Ile Glu Arg Tyr Phe Gln Ser Phe Pro Lys Val
        690                 695                 700
Arg Ala Trp Ile Glu Lys Thr Leu Glu Glu Gly Arg Lys Arg Gly Tyr
705                 710                 715                 720
Val Glu Thr Leu Phe Gly Arg Arg Tyr Val Pro Asp Leu Asn Ala
                725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Lys
        755                 760                 765
Leu Phe Pro Arg Leu Arg Glu Met Gly Ala Arg Met Leu Leu Gln Val
        770                 775                 780
```

His Asp Glu Leu Leu Leu Glu Ala Pro Gln Ala Arg Ala Glu Glu Val
785                 790                 795                 800

Ala Ala Leu Ala Lys Glu Ala Met Glu Lys Ala Tyr Pro Leu Ala Val
            805                 810                 815

Pro Leu Glu Val Glu Val Gly Ile Gly Glu Asp Trp Leu Ser Ala Lys
        820                 825                 830

Gly

<210> SEQ ID NO 3
<211> LENGTH: 2502
<212> TYPE: DNA
<213> ORGANISM: Artificial
<220> FEATURE:
<223> OTHER INFORMATION: Synthetic Polymerase

<400> SEQUENCE: 3

| | |
|---|---|
| atggcgatgc ttcccctctt tgagcccaaa ggccgggtcc tcctggtgga cggccaccac | 60 |
| ctggcctacc gcaccttctt cgccctgaag ggcctcacca cgagccgggg cgaaccggtg | 120 |
| caggcggtct acggcttcgc caagagcctc ctcaaggccc tgaaggagga cgggtacaag | 180 |
| gccgtcttcg tggtctttga cgccaaggcc cctccttcc gccacgaggc ctacgaggcc | 240 |
| tacaaggcgg ggagggcccc gacccccgag gacttccccc ggcagctcgc cctcatcaag | 300 |
| gagctggtgg acctcctggg gtttaccgt ctcgaggtcc ccggctacga ggcggacgac | 360 |
| gttctcgcca ccctggccaa gaaggcggaa aaggaggggt acgaggtgcg catcctcacc | 420 |
| gccgaccgcg acctctacca actcgtctcc gaccgcgtcg ccgtcctcca ccccgagggc | 480 |
| cacctcatca ccccggagtg gctttgggag aagtacggcc tcaggccgga gcagtgggtg | 540 |
| gacttccgcg ccctcgtggg ggaccccctcc gacaacctcc ccggggtcaa gggcatcggg | 600 |
| gagaagaccg ccctcaagct cctcaaggag tggggaagcc tggaaaacct cctcaagaac | 660 |
| ctggaccggg taaagccaga aaacgtccgg gagaagatca aggcccacct ggaagacctc | 720 |
| aggctctcct ggagctctc ccgggtgcgc accgacctcc cctggaggt ggacctcgcc | 780 |
| caggggcggg agcccgaccg ggaaaaggctt agggccttc tggagaggct tgagtttggc | 840 |
| agcctcctcc acgagttcgg ccttctggaa gccccaagg ccctggagga ggccccctgg | 900 |
| cccccgccgg aaggggcctt cgtgggcttt gtgctttccc gcaaggcgcc catgtgggcc | 960 |
| gatcttctgg ccctggccgc cgccaggggt ggtcgggtct accgggcccc cgagccttat | 1020 |
| aaagccctca gggacttgaa ggaggcgcgg gggcttctcg ccaaagacct gagcgttctg | 1080 |
| gccctaaggg aaggccttgg cctcccgccc ggcgacgacc ccatgctcct cgcctacctc | 1140 |
| ctggaccctt ccaacaccac ccccgagggg gtggcccggc gctacggcgg ggagtggacg | 1200 |
| gaggaggcgg gggagcgggc cgcccttttcc gagaggctct cgccaacct gtggggagg | 1260 |
| cttgaggggg aggagaggct cctttggctt taccggagg tggataggcc cctttccgct | 1320 |
| gtcctggccc acatggaggc cacaggggtg cgcctgacg tggcctatct cagggccttg | 1380 |
| tccctggagg tggccgagga gatcgcccgc ctcgaggccg aggtcttccg cctggccggc | 1440 |
| caccccttca acctcaactc ccgggaccag ctggaaaggg tcctctttga cgagctaggg | 1500 |
| cttcccgcca tcggcaagac ggagaagacc ggcaagcgct ccaccagcgc cgccgtcctg | 1560 |
| gaggccctcc gcgaggccca ccccatcgtg gagaagatct gcagtaccgg gagctcacc | 1620 |
| aagctgaaga gcacctacat tgaccccttg ccggacctca tccaccccag gacgggccgc | 1680 |
| ctccacaccc gcttcaacca gacggccacg gccacgggca ggctaagtag ctccgatccc | 1740 |

```
aacctccaga acatccccgt ccgcaccccg ctcgggcaga ggatccgccg ggccttcatc    1800
gctgaggagg ggtggctatt ggtggtcctg gactatagcc agatagagct cagggtgctg    1860
gcccacctct ccggcgacga gaacctgatc cgggtcttcc aggaggggcg ggacatccac    1920
acggaaaccg ccagctggat gttcggcgtc ccccggagg ccgtggaccc cctgatgcgc    1980
cgggcggcca agaccatcaa cttcgggggtt ctctacggca tgtcggccca ccgcctctcc    2040
caggagctag ccatccctta cgaggaggcc cgggccttca ttgagcgcta ctttcagagc    2100
ttccccaagg tgcgggcctg gattgagaag accctggagg agggcaggag gcggggggtac    2160 gtggagaccc tcttcggccg ccgccgctac gtgccagacc tagaggcccg ggtgaagagc    2220
gtgcgggagg cggccgagcg catggccttc aacatgcctg tccagggcac cgccgccgac    2280
ctcatgaagc tggctatggt gaagctcttc cccaggctgg aggaaacggg ggccaggatg    2340
ctccttcagg tccacgacga gctggtcctc gagaccccaa agagagggc ggaggccgtg    2400 gcccggctgg ccaaggaggt catggagggg gtgtatcccc tggccgtgcc cctggaggtg    2460
gaggtgggga taggggagga ctggctctcc gccaaggagt ga                       2502
```

<210> SEQ ID NO 4
<211> LENGTH: 833
<212> TYPE: PRT
<213> ORGANISM: Artificial
<220> FEATURE:
<223> OTHER INFORMATION: Synthetic Polymerase

<400> SEQUENCE: 4

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220
```

-continued

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
            245                 250                 255

Val Asp Leu Ala Gln Gly Arg Glu Pro Asp Arg Glu Arg Leu Arg Ala
        260                 265                 270

Phe Leu Glu Arg Leu Glu Phe Gly Ser Leu Leu His Glu Phe Gly Leu
    275                 280                 285

Leu Glu Ser Pro Lys Ala Leu Glu Glu Ala Pro Trp Pro Pro Pro Glu
290                 295                 300

Gly Ala Phe Val Gly Phe Val Leu Ser Arg Lys Ala Pro Met Trp Ala
305                 310                 315                 320

Asp Leu Leu Ala Leu Ala Ala Arg Gly Gly Arg Val Tyr Arg Ala
                325                 330                 335

Pro Glu Pro Tyr Lys Ala Leu Arg Asp Leu Lys Glu Ala Arg Gly Leu
        340                 345                 350

Leu Ala Lys Asp Leu Ser Val Leu Ala Leu Arg Glu Gly Leu Gly Leu
            355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Asp Arg Pro Leu Ser Ala Val Leu Ala His Met Glu Ala Thr
        435                 440                 445

Gly Val Arg Leu Asp Val Ala Tyr Leu Arg Ala Leu Ser Leu Glu Val
    450                 455                 460

Ala Glu Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
    530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Ile Ala Glu Glu Gly Trp Leu Leu Val
        595                 600                 605

Val Leu Asp Tyr Ser Gln Ile Glu Leu Arg Val Leu Ala His Leu Ser
    610                 615                 620

Gly Asp Glu Asn Leu Ile Arg Val Phe Gln Glu Gly Arg Asp Ile His
625                 630                 635                 640

Thr Glu Thr Ala Ser Trp Met Phe Gly Val Pro Arg Glu Ala Val Asp

```
            645                 650                 655
Pro Leu Met Arg Arg Ala Ala Lys Thr Ile Asn Phe Gly Val Leu Tyr
            660                 665                 670

Gly Met Ser Ala His Arg Leu Ser Gln Glu Leu Ala Ile Pro Tyr Glu
            675                 680                 685

Glu Ala Arg Ala Phe Ile Glu Arg Tyr Phe Gln Ser Phe Pro Lys Val
            690                 695                 700

Arg Ala Trp Ile Glu Lys Thr Leu Glu Glu Gly Arg Arg Gly Tyr
705                 710                 715                 720

Val Glu Thr Leu Phe Gly Arg Arg Tyr Val Pro Asp Leu Glu Ala
                    725                 730                 735

Arg Val Lys Ser Val Arg Glu Ala Ala Glu Arg Met Ala Phe Asn Met
                740                 745                 750

Pro Val Gln Gly Thr Ala Ala Asp Leu Met Lys Leu Ala Met Val Lys
                755                 760                 765

Leu Phe Pro Arg Leu Glu Glu Thr Gly Ala Arg Met Leu Leu Gln Val
            770                 775                 780

His Asp Glu Leu Val Leu Glu Thr Pro Lys Glu Arg Ala Glu Ala Val
785                 790                 795                 800

Ala Arg Leu Ala Lys Glu Val Met Glu Gly Val Tyr Pro Leu Ala Val
                    805                 810                 815

Pro Leu Glu Val Glu Val Gly Ile Gly Glu Asp Trp Leu Ser Ala Lys
            820                 825                 830

Glu

<210> SEQ ID NO 5
<211> LENGTH: 2499
<212> TYPE: DNA
<213> ORGANISM: Artificial
<220> FEATURE:
<223> OTHER INFORMATION: Synthetic Polymerase

<400> SEQUENCE: 5
atgcgtggta tgcttcctct ttttgagccc aagggccgcg tcctcctggt ggacggccac      60
cacctggcct accgcacctt ccacgccctg aagggcctca ccaccagccg ggggagccg     120 gtgcaggcgg tctacggctt cgccaagagc ctcctcaagg tcctcaagga ggacggggac     180
gcggtgatcg tggtctttga cgccaaggcc cctccttcc gccacgaggc ctacgggggg      240
tacaaggcgg ccgggcccc acgccggag actttcccc ggcaactcgc cctcatcaag        300
gagctggtgg acctcctggg gctggcgcgc tcgaggtcc cgggctacga ggcggacgac      360
gtcctggcca gctggccaa gaaggcggaa aaggagggct acgaggtccg catcctcacc      420
gccgacaaag accttacca gctcctttcc gaccgcatcc acgtcctcca ccccgagggg     480
tacctcatca ccccggcctg gctttgggaa agtacggcc tgaggcccga ccagtgggcc      540
gactaccggg ccctgaccgg ggacgagtcc gacaacttc cgggtcaa gggcatcggg        600 gagaagacgg cgaggaagct tctggaggag tgggggagcc tggaagccct cctcaagaac     660
ctggaccggc tgaagcccgc catccgggag aagatcctgg cccacatgga cgatctgaag     720
ctctcctggg acctggccaa ggtgcgcacc gacctgcccc tggaggtgga cttcgccaaa     780
aggcgggagc ccgaccggga gaggcttagg gcctttctgg agaggcttga gtttggcagc     840
ctcctccacg agttcggcct tctggaaagc cccaaggccc tggaggaggc ccctggcccc     900
ccgccggaag gggccttcgt gggctttgtg ctttcccgca aggagcccat gtgggccgat     960
```

```
cttctggctc tggccgccgc caggggggc cgggtccacc gggcccccga gccttataaa    1020
gccctcaggg acctgaagga ggcgcggggg cttctcgcca aagacctgag cgttctggcc    1080
ctgagggaag gccttggcct cccgcccggc gacgacccca tgctcctcgc ctacctcctg    1140
gaccctccca acaccacccc cgaggggggtg ccccggcgct acggcgggga gtggacggag    1200
gaggcgggg agcgggccgc cctttccgag aggctcttcg ccaacctgtg ggggaggctt    1260
gaggggagg agaggctcct ttggctttac cgggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct caaccagac ggccacggcc acggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggaccccct gatgcgccgg    1980
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg    2160
gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggagggggtg tatcccctgg ccgtgcccct ggaggtggag    2460
gtggggatag gggaggactg gctttccgcc aagggttag                           2499
```

<210> SEQ ID NO 6
<211> LENGTH: 832
<212> TYPE: PRT
<213> ORGANISM: Artificial
<220> FEATURE:
<223> OTHER INFORMATION: Synthetic Polymerase

<400> SEQUENCE: 6

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Val Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

```
Ala Leu Ile Lys Glu Leu Val Asp Leu Gly Leu Ala Arg Leu Glu
             100                 105                 110

Val Pro Gly Tyr Glu Ala Asp Val Leu Ala Ser Leu Ala Lys Lys
             115                 120                 125

Ala Glu Lys Glu Gly Tyr Glu Val Arg Ile Leu Thr Ala Asp Lys Asp
             130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                 165                 170                 175

Asp Gln Trp Ala Asp Tyr Arg Ala Leu Thr Gly Asp Glu Ser Asp Asn
             180                 185                 190

Leu Pro Gly Val Lys Gly Ile Gly Glu Lys Thr Ala Arg Lys Leu Leu
             195                 200                 205

Glu Glu Trp Gly Ser Leu Glu Ala Leu Leu Lys Asn Leu Asp Arg Leu
             210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                 245                 250                 255

Asp Phe Ala Lys Arg Arg Glu Pro Asp Arg Glu Arg Leu Arg Ala Phe
             260                 265                 270

Leu Glu Arg Leu Glu Phe Gly Ser Leu Leu His Glu Phe Gly Leu Leu
             275                 280                 285

Glu Ser Pro Lys Ala Leu Glu Glu Ala Pro Trp Pro Pro Glu Gly
             290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                 325                 330                 335

Glu Pro Tyr Lys Ala Leu Arg Asp Leu Lys Glu Ala Arg Gly Leu Leu
             340                 345                 350

Ala Lys Asp Leu Ser Val Leu Ala Leu Arg Glu Gly Leu Gly Leu Pro
             355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                 405                 410                 415

Trp Gly Arg Leu Glu Gly Glu Glu Arg Leu Leu Trp Leu Tyr Arg Glu
             420                 425                 430

Val Glu Arg Pro Leu Ser Ala Val Leu Ala His Met Glu Ala Thr Gly
             435                 440                 445

Val Arg Leu Asp Val Ala Tyr Leu Arg Ala Leu Ser Leu Glu Val Ala
             450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                 485                 490                 495

Glu Leu Gly Leu Pro Ala Ile Gly Lys Thr Glu Lys Thr Gly Lys Arg
             500                 505                 510
```

```
Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Gly
            820                 825                 830

<210> SEQ ID NO 7
<211> LENGTH: 2499
<212> TYPE: DNA
<213> ORGANISM: Artificial
<220> FEATURE:
<223> OTHER INFORMATION: Synthetic Polymerase

<400> SEQUENCE: 7
atggcgatgc ttcccctctt tgagcccaaa ggccgggtcc tcctggtgga cggccactac      60
ctggcctacc gcaccttctt cgccctgaag ggcctcacca cgagccgggg cgaaccggtg     120
caggcggtct acggcttcgc caagagcctc ctcaaggccc tgaaggagga cgggtacaag     180
gccgtcttcg tggtctttga cgccaaggcc cctccttcc gccacgaggc ctacgaggcc     240
tacaaggcgg ggagggcccc gacccccgag gacttccccc ggcagctcgc cctcatcaag     300
```

```
gagctggtgg acctcctggg gtttacccgc ctcgaggtcc ccggctacga ggcggacgac    360
gttctcgcca ccctggccaa gaaggcggaa aaggaggggt acgaggtgcg catcctcacc    420
gccgaccgtg acctctacca actcgtctcc gaccgcgtcg ccgtcctcca ccccgagggc    480
cacctcatca ccccggagtg gctttgggag aagtacggcc tcaggccgga gcagtgggtg    540
gacttccgcg ccctcgtggg ggaccccctcc gacaacctcc ccggggtcaa gggcatcggg    600
gagaagaccg ccctcaagct cctcaaggag tggggaagcc tggaaaacct cctcaagaac    660
ctggaccggc tgaagcccgc catccgggag aagatcctgg cccacatgga cgatctgaag    720
ctctcctggg acctggccaa ggtgcgcacc gacctgcccc tggaggtgga cttcgccaaa    780
aggcgggagc ccgaccggga gaggcttagg gcctttctgg agaggcttga gtttggcagc    840
ctcctccacg agttcggcct tctggaaagc cccaaggccc tggaggaggc cccctggccc    900
ccgccggaag gggccttcgt gggctttgtg ctttcccgca aggagcccat gtgggccgat    960
cttctggccc tggccgccgc caggggggc cgggtccacc gggcccccga gccttacaaa   1020
gccctcaggg acctgaagga ggcgcggggg cttctcgcca aagacctgag cgttctggcc   1080
ctgagggaag gccttggcct cccgccggc gacgaccca tgctcctcgc ctacctcctg   1140 gaccttcca acaccacccc cgaggggtg gcccggcgct acggcgggga gtggacggag   1200 gaggcgggg agcgggccgc cctttccgag aggctcttcg ccaacctgtg ggggaggctt   1260
gagggggagg agaggctcct ttggctttac cgggaggtgg agaggcccct ttccgctgtc   1320
ctggcccaca tggaggccac ggggtgcgc ctggacgtgg cctatctcag ggccttgtcc   1380
ctggaggtgg ccgaggagat cgcccgcctc gaggccgagg tcttccgcct ggccggccac   1440
cccttcaacc tcaactcccg ggaccagctg gaaagggtcc tctttgacga gctagggctt   1500
cccgccatcg gcaagacgga gaagaccggc aagcgctcca ccagcgccgc cgtcctggag   1560
gccctccgcg aggcccaccc catcgtggag aagatcctgc agtaccggga gctcaccaag   1620
ctgaagagca cctacattga cccccttgccg gacctcatcc accccaggac gggccgcctc   1680
cacacccgct caaccagac ggccacggcc acgggcaggc taagtagctc cgatcccaac   1740
ctccagaaca tccccgtccg cacccccgctt gggcagagga tccgccgggc cttcatcgcc   1800
gaggaggggt ggctattggt ggccctggac tatagccaga tagagctcag ggtgctggcc   1860
cacctctctg gcgacgagaa cctgatccgg gtcttccagg aggggcggga catccacacg   1920
gagaccgcca gctgggtgtt cggcgtcccc cgggaggccg tggacccct gatgcgccgg   1980 gcggccaaga ccatcaactt cggggtcctc tacggcatgt cggcccaccg cctctcccag   2040
gagctagcca tcccttacga ggaggcccag gccttcattg agcgctactt ccagagcttc   2100
cccaaggtgc gggcctggat tgagaagacc ctggaggagg caggaggcg ggggtacgtg   2160 gagaccctct tcggccgccg ccgctacgtg ccagacctag aggcccgggt gaagagcgtg   2220 cgggaggcg ccgagcgcat ggccttcaac atgcccgtcc agggcaccgc cgccgacctc   2280
atgaagctgg ctatggtgaa gctcttcccc aggctggagg aaatgggggc aggatgctc   2340 cttcaggtcc acgacgagct ggtcctcgag gccccaaaag agagggcgga ggccgtggcc   2400
cggctggcca aggaggtcct ggaggggtg tatcccctgg ccgtgcccct ggaggtggag   2460
gtggggatag ggaggactg gctctccgcc aaggagtga                           2499
```

<210> SEQ ID NO 8
<211> LENGTH: 832
<212> TYPE: PRT

<213> ORGANISM: Artificial
<220> FEATURE:
<223> OTHER INFORMATION: Synthetic Polymerase

<400> SEQUENCE: 8

```
Met Ala Met Leu Pro Leu Phe Glu Pro Lys Gly Arg Val Leu Leu Val
1               5                   10                  15

Asp Gly His Tyr Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Pro Gly Tyr Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
```

-continued

```
            385                 390                 395                 400
        Glu Ala Gly Glu Arg Ala Ala Leu Ser Glu Arg Leu Phe Ala Asn Leu
                        405                 410                 415
        Trp Gly Arg Leu Glu Gly Glu Arg Leu Leu Trp Leu Tyr Arg Glu
                        420                 425                 430
        Val Glu Arg Pro Leu Ser Ala Val Leu Ala His Met Glu Ala Thr Gly
                        435                 440                 445
        Val Arg Leu Asp Val Ala Tyr Leu Arg Ala Leu Ser Leu Glu Val Ala
                        450                 455                 460
        Glu Glu Ile Ala Arg Leu Glu Ala Glu Val Phe Arg Leu Ala Gly His
        465                 470                 475                 480
        Pro Phe Asn Leu Asn Ser Arg Asp Gln Leu Glu Arg Val Leu Phe Asp
                        485                 490                 495
        Glu Leu Gly Leu Pro Ala Ile Gly Lys Thr Glu Lys Thr Gly Lys Arg
                        500                 505                 510
        Ser Thr Ser Ala Ala Val Leu Glu Ala Leu Arg Glu Ala His Pro Ile
                        515                 520                 525
        Val Glu Lys Ile Leu Gln Tyr Arg Glu Leu Thr Lys Leu Lys Ser Thr
                        530                 535                 540
        Tyr Ile Asp Pro Leu Pro Asp Leu Ile His Pro Arg Thr Gly Arg Leu
        545                 550                 555                 560
        His Thr Arg Phe Asn Gln Thr Ala Thr Ala Thr Gly Arg Leu Ser Ser
                        565                 570                 575
        Ser Asp Pro Asn Leu Gln Asn Ile Pro Val Arg Thr Pro Leu Gly Gln
                        580                 585                 590
        Arg Ile Arg Arg Ala Phe Ile Ala Glu Glu Gly Trp Leu Leu Val Ala
                        595                 600                 605
        Leu Asp Tyr Ser Gln Ile Glu Leu Arg Val Leu Ala His Leu Ser Gly
                        610                 615                 620
        Asp Glu Asn Leu Ile Arg Val Phe Gln Glu Gly Arg Asp Ile His Thr
        625                 630                 635                 640
        Glu Thr Ala Ser Trp Val Phe Gly Val Pro Arg Glu Ala Val Asp Pro
                        645                 650                 655
        Leu Met Arg Arg Ala Ala Lys Thr Ile Asn Phe Gly Val Leu Tyr Gly
                        660                 665                 670
        Met Ser Ala His Arg Leu Ser Gln Glu Leu Ala Ile Pro Tyr Glu Glu
                        675                 680                 685
        Ala Gln Ala Phe Ile Glu Arg Tyr Phe Gln Ser Phe Pro Lys Val Arg
                        690                 695                 700
        Ala Trp Ile Glu Lys Thr Leu Glu Glu Gly Arg Arg Arg Gly Tyr Val
        705                 710                 715                 720
        Glu Thr Leu Phe Gly Arg Arg Arg Tyr Val Pro Asp Leu Glu Ala Arg
                        725                 730                 735
        Val Lys Ser Val Arg Glu Ala Ala Glu Arg Met Ala Phe Asn Met Pro
                        740                 745                 750
        Val Gln Gly Thr Ala Ala Asp Leu Met Lys Leu Ala Met Val Lys Leu
                        755                 760                 765
        Phe Pro Arg Leu Glu Glu Met Gly Ala Arg Met Leu Leu Gln Val His
                        770                 775                 780
        Asp Glu Leu Val Leu Glu Ala Pro Lys Glu Arg Ala Glu Ala Val Ala
        785                 790                 795                 800
        Arg Leu Ala Lys Glu Val Leu Glu Gly Val Tyr Pro Leu Ala Val Pro
                        805                 810                 815
```

Leu Glu Val Glu Val Gly Ile Gly Glu Asp Trp Leu Ser Ala Lys Glu
        820                 825                 830

<210> SEQ ID NO 9
<211> LENGTH: 2502
<212> TYPE: DNA
<213> ORGANISM: Artificial
<220> FEATURE:
<223> OTHER INFORMATION: Synthetic Polymerase

<400> SEQUENCE: 9

```
atggcgatgc ttcccctctt tgagcccaaa ggccgggtcc tcctggtgga cggccaccac      60
ctggcctacc gcaccttctt cgccctgaag ggcctcacca cgagccgggg cgaaccggtg     120
caggcggtct acggcttcgc caagagcctc ctcaaggccc tgaaggagga cgggtacaag     180
gccgtcttcg tggtctttga cgccaaggcc cctccttcc gccacgaggc ctacgaggcc      240
tacaaggcgg ggagggcccc gaccccccgag gacttccccc ggcagctcgc cctcatcaag     300
gagctggtgg acctcctggg gtttacccgc tcgaggtcc aaggctacga ggcggacgac      360
gtcctcgcca ccctggccaa gaaggcgaa aaagaagggt acgaggtgcg cgtcctcacc       420
gccgaccggg acctctacca gctcgtctcc gaccgcgtcg ccgtcctcca ccccgagggc     480
cacctcatca ccccggagtg gctttgggag aagtacggcc tcaggccgga gcagtgggtg     540
gacttccgcg ccctcgtggg ggaccccctcc gacaacctcc ccgggtcaa gggcatcggg      600
gagaagaccg ccctcaagct cctcaaggag tggggaagcc tggaaaatct cctcaagaac     660
ctggatcggg taaagccgga aaacgtccgg gagaagatca ggcccacct ggaagacctc      720
aggctctcct ggagctctc ccgggtgcgc accgacctcc cctggaggt ggacctcgcc       780
caggggcggg agcccgaccg ggaagggctt agggccttcc tggagaggct ggagttcggc     840
agcctcctcc atgagttcgg ccttctggaa agccccaagg ccctggagga ggcccccgtg     900
cccccgccgc aaggggcctt cgtgggcttt gtgctttccc gcaaggagcc catgtgggcc     960
gatcttctgg ccctggccgc cgccagggggg gccgggtcc accgggcccc cgagccttat    1020
aaagcccctca gggacctgaa ggaggcgcgg gggcttctcg ccaaagacct gagcgttctg    1080
gccctgaggg aaggccttgg cctcccgccc gccgacgacc ccatgctcct cgcctacctc    1140
ctggaccctt caacaccac cccgagggg gtggcccggc gctacggcgg ggagtggacg       1200
gaggaggcgg gggagcgggc cgcccttccc gagaggctct cgccaacct gtggggagg     1260
cttgagggg aggagaggct cctttggctt taccggagg tggagaggcc cctttccgct      1320
gccctggccc acatggaggc cacggggtg cgcctggacg tggcctatct cagggccttg     1380
tccctggagg tggccgagga atcgcccgc ctcgaggccg aggtcttccg cctgccggc      1440
caccccttca acctcaactc ccgggaccag ctggaaaggg tcctctttga cgagctaggg    1500
cttcccgcca tcggcaagac ggagaagacc ggcaagcgct ccaccagcgc cgccgtcctg    1560
gaggccctcc gcgaggccca ccccatcgtg gagaagatcc tgcagtaccg ggagctcacc    1620
aagctgaaga gcacctacat tgacccttg ccggacctca tccaccccag acgggccgc     1680
ctccacaccc gcttcaacca cggccacg gccacgggca ggctaagtag ctccgatccc     1740
aacctccaga acatccccgt ccgcacccg cttgggcaga ggatccgccg ggccttcatc    1800
gccgaggagg ggtggctatt ggtggccctg gactatagcc agatagagct cagggtgctg    1860
gcccacctct ccggcgacga gaacctgatc cgggtcttcc aggaggggcg ggacatccac    1920
acggagaccg ccagctggat gttcggcgtc ccccgggag ccgtggaccc cctgatgcgc   1980
```

-continued

```
cgggcggcca agaccatcaa cttcggggtc ctctacggca tgtcggccca ccgcctctcc     2040
caggagctag ccatccctta cgaggaggcc caggccctca ttgagcgcta cttccagagc     2100
ttccccaagg tgcgggcctg gattgagaag accctggagg agggcaggag gcggggtac     2160 gtggagaccc tcctcggccg ccgccgctac gtgccagacc tagaggcccg ggtgaagagc     2220
gtgcgggagg cggccgagcg catggccttc aacatgcccg tccagggcac cgccgccgac     2280
ctcatgaagc tggctatggt gaagctcttc cccaggctgg aggaaatggg ggccaggatg     2340
ctccttcagg tccacgacga gctggtcctc gaggccccaa agagagggc ggaggccgtg     2400 gcccggctgg ccaaggaggt catggagggg gtgtatcccc tggccgtgcc cctggaggtg     2460
gaggtgggga tagggagga ctggctctcc gccaaggagt ga                        2502
```

<210> SEQ ID NO 10
<211> LENGTH: 833
<212> TYPE: PRT
<213> ORGANISM: Artificial
<220> FEATURE:
<223> OTHER INFORMATION: Synthetic Polymerase

<400> SEQUENCE: 10

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Tyr Lys Ala Val Phe Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Phe Thr Arg Leu Glu
            100                 105                 110

Val Gln Gly Tyr Glu Ala Asp Asp Val Leu Ala Thr Leu Ala Lys Lys
        115                 120                 125

Ala Glu Lys Glu Gly Tyr Glu Val Arg Val Leu Thr Ala Asp Arg Asp
    130                 135                 140

Leu Tyr Gln Leu Val Ser Asp Arg Val Ala Val Leu His Pro Glu Gly
145                 150                 155                 160

His Leu Ile Thr Pro Glu Trp Leu Trp Glu Lys Tyr Gly Leu Arg Pro
                165                 170                 175

Glu Gln Trp Val Asp Phe Arg Ala Leu Val Gly Asp Pro Ser Asp Asn
            180                 185                 190

Leu Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp Arg Val
    210                 215                 220

Lys Pro Glu Asn Val Arg Glu Lys Ile Lys Ala His Leu Glu Asp Leu
225                 230                 235                 240

Arg Leu Ser Leu Glu Leu Ser Arg Val Arg Thr Asp Leu Pro Leu Glu
                245                 250                 255

Val Asp Leu Ala Gln Gly Arg Glu Pro Asp Arg Glu Gly Leu Arg Ala
            260                 265                 270
```

```
Phe Leu Glu Arg Leu Glu Phe Gly Ser Leu Leu His Glu Phe Gly Leu
        275                 280                 285
Leu Glu Ser Pro Lys Ala Leu Glu Glu Ala Pro Trp Pro Pro Pro Glu
        290                 295                 300
Gly Ala Phe Val Gly Phe Val Leu Ser Arg Lys Glu Pro Met Trp Ala
305                 310                 315                 320
Asp Leu Leu Ala Leu Ala Ala Arg Gly Gly Arg Val His Arg Ala
                325                 330                 335
Pro Glu Pro Tyr Lys Ala Leu Arg Asp Leu Lys Glu Ala Arg Gly Leu
                340                 345                 350
Leu Ala Lys Asp Leu Ser Val Leu Ala Leu Arg Glu Gly Leu Gly Leu
        355                 360                 365
Pro Pro Ala Asp Asp Pro Met Leu Leu Ala Tyr Leu Leu Asp Pro Ser
        370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Ala Leu Ser Glu Arg Leu Phe Ala Asn
                405                 410                 415
Leu Trp Gly Arg Leu Glu Gly Glu Glu Arg Leu Leu Trp Leu Tyr Arg
        420                 425                 430
Glu Val Glu Arg Pro Leu Ser Ala Ala Leu Ala His Met Glu Ala Thr
        435                 440                 445
Gly Val Arg Leu Asp Val Ala Tyr Leu Arg Ala Leu Ser Leu Glu Val
        450                 455                 460
Ala Glu Glu Ile Ala Arg Leu Glu Ala Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Ala Ile Gly Lys Thr Glu Lys Thr Gly Lys
                500                 505                 510
Arg Ser Thr Ser Ala Ala Val Leu Glu Ala Leu Arg Glu Ala His Pro
        515                 520                 525
Ile Val Glu Lys Ile Leu Gln Tyr Arg Glu Leu Thr Lys Leu Lys Ser
        530                 535                 540
Thr Tyr Ile Asp Pro Leu Pro Asp Leu Ile His Pro Arg Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Ile Ala Glu Glu Gly Trp Leu Leu Val
        595                 600                 605
Ala Leu Asp Tyr Ser Gln Ile Glu Leu Arg Val Leu Ala His Leu Ser
        610                 615                 620
Gly Asp Glu Asn Leu Ile Arg Val Phe Gln Glu Gly Arg Asp Ile His
625                 630                 635                 640
Thr Glu Thr Ala Ser Trp Met Phe Gly Val Pro Arg Glu Ala Val Asp
                645                 650                 655
Pro Leu Met Arg Arg Ala Ala Lys Thr Ile Asn Phe Gly Val Leu Tyr
                660                 665                 670
Gly Met Ser Ala His Arg Leu Ser Gln Glu Leu Ala Ile Pro Tyr Glu
        675                 680                 685
```

```
Glu Ala Gln Ala Leu Ile Glu Arg Tyr Phe Gln Ser Phe Pro Lys Val
    690                 695                 700
Arg Ala Trp Ile Glu Lys Thr Leu Glu Glu Gly Arg Arg Gly Tyr
705                 710                 715                 720
Val Glu Thr Leu Leu Gly Arg Arg Tyr Val Pro Asp Leu Glu Ala
                725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Lys
                755                 760                 765
Leu Phe Pro Arg Leu Glu Glu Met Gly Ala Arg Met Leu Leu Gln Val
    770                 775                 780
His Asp Glu Leu Val Leu Glu Ala Pro Lys Glu Arg Ala Glu Ala Val
785                 790                 795                 800
Ala Arg Leu Ala Lys Glu Val Met Glu Gly Val Tyr Pro Leu Ala Val
                805                 810                 815
Pro Leu Glu Val Glu Val Gly Ile Gly Glu Asp Trp Leu Ser Ala Lys
                820                 825                 830
Glu
```

<210> SEQ ID NO 11
<211> LENGTH: 23
<212> TYPE: DNA
<213> ORGANISM: Artificial
<220> FEATURE:
<223> OTHER INFORMATION: Synthetic Oligonucleotide Primer

<400> SEQUENCE: 11
aaaaatctag ataacgaggg caa                                           23

<210> SEQ ID NO 12
<211> LENGTH: 28
<212> TYPE: DNA
<213> ORGANISM: Artificial
<220> FEATURE:
<223> OTHER INFORMATION: Synthetic Oligonucleotide Primer

<400> SEQUENCE: 12
accaccgaac tgcgggtgac gccaagcg                                      28

<210> SEQ ID NO 13
<211> LENGTH: 45
<212> TYPE: DNA
<213> ORGANISM: Artificial
<220> FEATURE:
<223> OTHER INFORMATION: Synthetic Oligonucleotide Primer

<400> SEQUENCE: 13
gtaaaacgac ggccagtacc accgaactgc gggtgacgcc aagcg                   45

<210> SEQ ID NO 14
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 14
caggaaacag ctatgacaaa aatctagata acgagggcaa                         40

<210> SEQ ID NO 15

```
<211> LENGTH: 17
<212> TYPE: DNA
<213> ORGANISM: Artificial
<220> FEATURE:
<223> OTHER INFORMATION: Synthetic Oligonucleotide Primer

<400> SEQUENCE: 15
caggaaacag ctatgac                                                      17

<210> SEQ ID NO 16
<211> LENGTH: 17
<212> TYPE: DNA
<213> ORGANISM: Artificial
<220> FEATURE:
<223> OTHER INFORMATION: Synthetic Oligonucleotide Primer

<400> SEQUENCE: 16
gtaaaacgac ggccagt                                                      17

<210> SEQ ID NO 17
<211> LENGTH: 26
<212> TYPE: DNA
<213> ORGANISM: Artificial
<220> FEATURE:
<223> OTHER INFORMATION: Synthetic Oligonucleotide Primer

<400> SEQUENCE: 17
accaccgaac tgcgggtgac gccaag                                            26

<210> SEQ ID NO 18
<211> LENGTH: 25
<212> TYPE: DNA
<213> ORGANISM: Artificial
<220> FEATURE:
<223> OTHER INFORMATION: Synthetic Oligonucleotide Primer

<400> SEQUENCE: 18
gggtacgtgg agacctctt cggcc                                              25
```

POLYMERASE

CROSS-REFERENCE TO RELATED APPLICATIONS

This application is a divisional application of the U.S. national phase application U.S. Ser. No. 12/446,746 of International Application No. PCT/GB2007/004031, filed 23 Oct. 2007, incorporated by reference, which claims priority benefit of Great Britain Patent Application No. 0621094.2 filed Oct. 23, 2006 and Great Britain Patent Application No. 0623977.6 filed Nov. 30, 2006.

INCORPORATION BY REFERENCE OF MATERIALS SUBMITTED ELECTRONICALLY

This application contains, as a separate part of disclosure, a Sequence Listing in computer-readable form (filename: 44587A_SeqListing.txt; 54,871 byte—ASCII text file; created Feb. 18, 2013) which is incorporated by reference in its entirety.

FIELD OF THE INVENTION

The present invention relates to engineered polymerases. In particular, the invention relates to engineered polymerases that are resistant to certain environmental and biological inhibitors. Uses for said engineered polymerases and methods of generating said engineered polymerases are also described.

BACKGROUND TO THE INVENTION

Polymerase enzymes, such as DNA polymerase, RNA polymerase, or reverse transcriptase, can catalyse the formation of polynucleotides of DNA or RNA using an existing strand of DNA or RNA as a template. RNA polymerases and DNA polymerases can catalyse the polymerisation of RNA and DNA respectively using a DNA template, whereas reverse transcriptase can catalyse the formation of DNA using an RNA template.

DNA polymerases, for example are naturally occurring intracellular enzymes, and are used by a cell to replicate a nucleic acid strand using a template molecule to manufacture a complementary nucleic acid strand. DNA polymerases are also widely used in vitro for various biochemical applications including cDNA synthesis and DNA sequencing reactions, amplification of nucleic acids by methods such as the polymerase chain reaction (PCR) and for RNA transcription-medicated amplification methods.

The polymerase chain reaction (PCR) is a widely used technique that allows a specific region of DNA to be amplified exponentially, provided that at least part of its nucleotide sequence is already known. This known region of sequence is used to design synthetic DNA oligonucleotides complementary to each strand of the DNA double helix. These oligonucleotides serve as primers for in vitro DNA synthesis, which is catalyzed by DNA polymerase.

Unfortunately, the effectiveness of this technique in basic research or in forensic or clinical applications is limited by some technical problems. A number of substances are known that are potent inhibitors of polymerase activity and limit the use of polymerase chain reaction (PCR) in biological samples where they are present. Examples include heme (and its degradation products such as bilirubin) present in blood and faeces. Another potent inhibitor present in the environment is humic acid.

Humic acids are a complex mixture of polyphenolic acids produced by the decomposition of organic matter (e.g. decomposing terrestrial vegetation). Humic acids are ubiquitous in soil and water and thus are present in any sample exposed to the environment. Inhibition of PCR by humic acids is thus especially relevant for samples of paelontological, archaeological or forensic interest, which are exposed to soil for extended periods of time.

Some attempts have been made to circumvent the problem of humic acid contamination in PCR samples. One approach to the problem has been purification or extraction of DNA from samples in advance of PCR (LaMontagne et al (2002) J Microbiol Methods 49:255-64; Howeler et al J Microbiol Methods 2003 54:37-45). Unfortunately, humic acid contamination may still be a problem depending on the extraction method used (LaMontagne et al 2002). Furthermore, not all contaminants are completely removed during classical extraction protocols (such as detergent, protease and phenol-chloroform treatments), and loss of the original sample may occur. Another problem with extraction procedures includes the use of expensive materials such as ion-exchange columns, glass bead extraction, immunomagnetic separation, size-exclusion chromatography, anion-binding resins or spin columns (Wilson, I G (1997) Appl. Environ. Microbiol. 63:3741-3751). Moreover, the extra steps required in each PCR protocol may increase cross-contamination risks and subsequent false-positive results.

Another approach to tackle the inhibitory effect of humic acid on polymerase activity is to increase the concentration of polymerase in each reaction mixture (Sutlovic et al Croat Med J 2005 46:556-62). Various additives such as BSA, T4 gp32 or salmon sperm DNA are also reported to relieve inhibition of polymerase activity, but these need to be added at substantial concentrations (typically greater than 0.2 mg/ml) (Tebbe et al Appl Environ Microbiol. (1993) 59:2657-65).

With all previous attempts to avoid inhibition of PCR by humic acid—such as extraction techniques or the addition of supplements—extra time and expense is associated with the use of additional reagents or protocols.

There remains a need in the art for a simple and more effective way of dealing with the inhibitory effect of humic acid on DNA polymerases, particularly in PCR.

SUMMARY OF THE INVENTION

The present invention addresses the problem of inhibition of DNA polymerase activity by humic acid. Specifically, the present invention provides a DNA polymerase that is resistant to the inhibitory effects of humic acid. Importantly, the problem of humic acid intolerance encountered by DNA polymerase in PCR reactions is solved not by altering the amount or potency of humic acid present in a sample, as in the prior art, but via changes in the property of the polymerase itself.

Thus in a first aspect, the invention provides an engineered polymerase wherein that polymerase exhibits an enhanced ability to process nucleic acid in the presence of humic acid compared with wild type polymerase.

According to the above aspect of the invention, the term 'engineered polymerase' refers to a polymerase which has a nucleic acid sequence which is not 100% identical at the nucleic acid level to the one or more polymerase/s or fragments thereof, from which it is derived, and which is synthetic. According to the invention, the engineered polymerase may be derived from wild type DNA polymerase by the substitution, deletion or insertion of one or more amino acids. The term 'engineered polymerase' also includes within its scope fragments, derivatives and homologues of an 'engineered polymerase' as herein defined so long as it exhibits the requisite property of possessing an enhanced ability to process nucleic acid in the presence of humic acid compared to that of wild type polymerase.

A "wild-type" polymerase is a polymerase which has not been engineered in accordance with the present invention. Preferably, a wild-type polymerase is the polymerase which is subjected to the claimed engineering procedure; thus, the wild-type polymerase is unmodified form of the engineered polymerase.

"Enhanced ability" is taken to mean an increase in any function of engineered polymerase that enables it to process nucleic acid, as compared to that of wild type polymerase. This includes an increase in the ability of polymerase to catalyze formation of a bond between the 3' hydroxyl group at the growing end of a nucleic acid primer and the 5' phosphate group of a nucleotide triphosphate. Functions of DNA polymerases also include but are not limited to, incorporation of deoxyribonucleotide subunits or derivatives thereof, phosphoryl transfer, translocation along a DNA template, extension of primer substrates, template recognition and replication or amplification of template DNA.

An engineered polymerase according to the invention may be a DNA polymerase. A DNA polymerase will be known to those in the art and the function and properties of which will be well known. An engineered DNA polymerase will have similar properties and characteristics to the engineered polymerase of the invention in that they will have an enhanced ability to process nucleic acid compared to the wild type DNA polymerases from which they may have been derived.

The engineered DNA polymerase isolated by the present inventors has an enhanced ability to process nucleic acid at concentrations of between 0.1% and 50% humic acid. Preferably, the engineered DNA polymerase has an enhanced ability to process nucleic acid at concentrations of between 1 and 30% humic acid. Most preferably, the engineered DNA polymerase has an enhanced ability to process nucleic acid at concentrations of between 5 and 20% humic acid. Humic acid may be derived from decomposed organic material such as peat soil. Methods for the derivation of a solution of humic acid at concentrations of between 5 and 20% are enclosed herein. Using these methods those skilled in the art would be able to determine other polymerases that can process nucleic acids at different concentrations of humic acid that are within the scope of this invention. The present inventors measure the ability of engineered DNA polymerase to process nucleic acid by comparing the activity of engineered DNA polymerase to wild type DNA polymerase at various concentrations of humic acid. Engineered DNA polymerases can then be identified that are active under humic acid concentrations where wild type DNA polymerases are not.

Engineered DNA polymerases of the present invention are found to be active at least 2, 3, 4, 5, 6, 7, 8, 9, 10, 11, 12, 13, 14, 15, 16, 17, 18, 19 or 20 fold greater concentrations of humic acid than concentrations under which wild type DNA polymerase is still active. Accordingly there is provided an engineered DNA polymerase with an enhanced ability to process nucleic acid in the presence of humic acid wherein said ability is enhanced 2, 3, 4, 5, 6, 7, 8, 9, 10, 11, 12, 13, 14, 15, 16, 17, 18, 19 or 20 fold when compared to wild type DNA polymerase.

Engineered DNA polymerases of the present invention may be used in any in vitro reaction wherein the property of humic acid resistance is regarded as beneficial. DNA polymerases are used in many in vitro molecular biology applications including mutagenesis, cDNA libraries, sequencing and polymerase chain reaction (PCR). It is known that inhibition of wild type DNA polymerase activity by humic acid can inhibit or impair a polymerase chain reaction (PCR). Central to this technique is the activity of DNA polymerase, which is involved in replicating template DNA at sites marked by primers, by incorporating deoxyribonucleotide subunits to synthesise a new DNA strand. Biological samples of paelontological, archaeological or forensic interest containing template DNA, may be exposed to soil for extended periods of time and may contain humic acid. The engineered DNA polymerases of the present invention are particularly suitable for use in PCR reactions performed on such samples. Therefore, preferably, the engineered DNA polymerase of the present invention has an enhanced ability to process nucleic acid within a polymerase chain reaction.

Nucleic acid molecules encoding engineered DNA polymerases of the present invention can readily be obtained in a variety of ways including, without limitation, chemical synthesis, cDNA or genomic library screening, expression library screening, and/or PCR amplification of cDNA.

The present inventors also provide methods for the introduction of mutations into nucleic acid and for generation of libraries thereof. Those skilled in the art will be aware of several techniques to generate diversity within a gene or within nucleic acid. Nucleic acid molecules encoding variants may be produced using site directed mutagenesis, error prone PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

The present inventors describe generation of a library of chimeric polymerase gene variants that can be derived by a gene shuffling technique such as "staggered extension process" (StEP) (Zhao et al Biotechnol (1998) 16:258-261). This technique allows two or more genes of interest from different species to be randomly recombined to produce chimeras, the sequence of which contains parts of the original input parent genes.

Accordingly, there is provided in the present invention, an engineered DNA polymerase comprising a DNA polymerase that is generated from a library derived by recombining related wild type DNA polymerase genes. Advantageously, an engineered DNA polymerase with humic acid resistance according to the invention is derived from a pol A-family DNA polymerase. Preferably, the wild type DNA polymerase is selected from a group consisting of Taq, T8 (a previously selected 11 fold more thermostable Taq variant; Ghadessey et al. 2001), TTh (*Thermus thermophilus*) and Ttl (*Thermus flavus*).

There is also provided in the present invention, an engineered DNA polymerase generated from a library of nucleic acids derived by error prone polymerase chain reaction mutagenesis and/or recombination of related wild type DNA polymerase genes.

In a second aspect of the invention, there are provided methods for the generation of engineered DNA polymerases that are humic acid resistant. Accordingly, there is provided a method for producing a DNA polymerase of the present invention which comprises:

(a) preparing a nucleic acid molecule encoding a DNA polymerase;
(b) introducing a mutation into the nucleic acid molecule encoding that polymerase according to step (a) so that one or more nucleotides in one or more regions are not identical to the DNA polymerase from which it is derived;

(c) selecting a modified DNA polymerase expressed by the mutated nucleic acid molecule; and
(d) isolating and purifying that DNA polymerase.

A highly preferred method of generating engineered DNA polymerases of the present invention is by directed evolution. The techniques of directed evolution and compartmentalised self replication are detailed in GB 97143002 and GB 98063936 and GB 01275643, in the name of the present inventors. These documents are herein incorporated by reference.

The inventors modified the methods of compartmentalised self replication and surprisingly generated DNA polymerases which exhibited humic acid resistance. Accordingly, in a further aspect of the invention, there is provided a method for the generation of an engineered DNA polymerase which comprises the steps of:
a) providing a pool of nucleic acids comprising members each encoding an engineered DNA polymerase;
b) providing humic acid;
c) subdividing the pool of nucleic acids into compartments, such that each compartment comprises substantially a nucleic acid member of the pool together with the engineered DNA polymerase or variant encoded by the nucleic acid member, and humic acid;
d) allowing processing of the nucleic acid member to occur; and
e) detecting processing of the nucleic acid member by that engineered DNA polymerase; and
f) optionally repeating the series of steps (a) to (f) one or more times.

Preferably, the processing of said nucleic acid member is part of a polymerase chain reaction.

Preferably, humic acid is provided at a concentration that inhibits wild type DNA polymerase activity. Advantageously, humic acid is added at a concentration sufficient to provide a selection pressure, but not so great that all polymerase activity is inhibited. Using the above method of generating an engineered DNA polymerase, only those DNA polymerases that are resistant to a given amount of humic acid will be able to process nucleic acid and subsequently be detected.

In another aspect of the above method, the member comprises a bacterial cell expressing an engineered DNA polymerase according to the present invention. Preferably the bacterial cell is *E. Coli*.

In the above method of generating an engineered DNA polymerase, only those DNA polymerases which exhibit at least some resistance to humic acid will be able to process nucleic acid and subsequently be detected. Accordingly, the post-amplification copy number of the nucleic acid member which encodes engineered DNA polymerase according to the invention, is substantially proportional to the activity of the DNA polymerase. Preferably, nucleic acid processing is detected by assaying the copy number of the nucleic acid member.

In a preferred embodiment, the compartments consist of the encapsulated aqueous component of a water-in-oil emulsion. The water-in-oil emulsion is preferably produced by emulsifying an aqueous phase with an oil phase in the presence of a surfactant comprising 4.5% v/v Span 80, 0.4% v/v Tween 80 and 0.1% v/v Triton X100, or a surfactant comprising Span 80, Tween 80 and Triton X100 in substantially the same proportions. Preferably, the water:oil phase ratio is 1:2, which leads to adequate droplet size. Such emulsions have a higher thermal stability than more oil-rich emulsions.

In a further aspect of the invention, there is provided an engineered DNA polymerase characterized in that the amino acid sequence of that polymerase comprises, preferably consists of, the amino acid sequence designated herein as SEQ ID NO: 2.

There is also provided an isolated nucleic acid molecule which encodes an engineered DNA polymerase polypeptide comprising an amino acid sequence having at least 80% identity to any of SEQ ID NOs 2, 4 or 6 and wherein said polypeptide has DNA polymerase activity in the presence of 5 to 20% humic acid. Preferably, said polypeptide has at least 90% identity to amino residues of SEQ ID NO: 2, 4 or 6. More preferably, said polypeptide has at least 95% identity to amino residues of SEQ ID NO: 2, 4 or 6. Most preferably, said polypeptide has at least 99% identity to residues of SEQ ID NO: 2, 4 or 6.

In a further embodiment of the invention, there is provided an isolated nucleic acid molecule encoding an engineered DNA polymerase according to the present invention comprising a nucleotide sequence as set forth in SEQ ID NO. 1, 3, or 5. Preferably, the isolated nucleic acid molecule comprises a nucleotide sequence having at least 90% sequence identity with SEQ ID NO. 1, 3 or 5

There is also provided in the present invention, an engineered DNA polymerase wherein said engineered DNA polymerase has at least 80% identity to amino residues of the wild type polymerase. Preferably, said engineered DNA polymerase has at least 90% identity to amino residues of the wild type polymerase. Most preferably, said engineered DNA polymerase has at least 95% identity to amino residues of the wild type polymerase. Preferably, said wild type DNA polymerase is a Pol A family DNA polymerase. Advantageously said wild type DNA polymerase is selected from the group comprising Taq, T8, TTh and Ttl DNA polymerases.

Preferably an engineered DNA polymerase of the present invention has at least 95% amino acid sequence homology and at least 95% of the proof-reading capability and thermostability of wild type DNA polymerase isolated from *Thermus aquaticus*, *Thermus thermophilus*, or *Thermus flavus*.

In a further aspect of the invention, there is provided, a nucleotide sequence encoding the polypeptides described above. There is also provided, a recombinant nucleic acid molecule comprising a promoter sequence operably linked to nucleic acid molecule in which said promoter sequence can be constitutive, inducible, or tissue-specific in function. There is furthermore provided a cell transformed with said recombinant nucleic acid molecule. Host cells may be prokaryotic host cells (such as *E. coli*) or eukaryotic host cells (such as yeast, insect, or vertebrate cells). Preferably, the host cell is a bacterial host cell. Most preferably the host cell is *E. coli*.

Advantageously, the polypeptide described above is used for producing primer extension products. Preferably, the engineered DNA polymerase of the present invention is used in a polymerase chain reaction.

In a further aspect still, there is provided a kit for amplifying DNA comprising an isolated, engineered DNA polymerase of the present invention.

DETAILED DESCRIPTION OF THE INVENTION

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, e.g., J. Sambrook, E. F. Fritsch, and T. Maniatis, 1989, Molecular Cloning: A Laboratory Manual, Second Edition, Books 1-3, Cold Spring Harbor Laboratory Press; B.

Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts are herein incorporated by reference.

Humic Acid

Humic acid is a complex substance found in certain deposits of partially decomposed organic matter, particularly dead plants (Hertkom N. et al. 2002). These deposits exist especially in previously heavily forested areas with moist, swamp-like conditions. The deposits represent a stage between decaying vegetation (humus/humates/peat) and eventual potential formation of coal and oil.

The term "humic acid" refers to any of various organic acids obtained from humus wherein humus is partially decomposed organic matter. Other terms that are used for humic acid include but are not limited to humin, humic substance, natural organic matter, fulvic acid, moor, ulmin, gein, ulmic or geic acid. Humic substances are endowed with acidic functional groups mainly carboxylic acid, which confer on these molecules the ability to chelate multivalent cations such as $Mg^{2+}$, $Ca^{2+}$, and $Fe^{2+}$. Humic acid contains a diverse array of relatively low molecular weight entities including metals, aliphatic acids, ethers, esters, alcohols, phenols (carbolic acids), phenolic compounds, aromatic lignin derived fragments, polysaccharides and polypeptides (Simpson A J et al. 2002). Additional consulting references include Flaig, Soil Components pp. 1-219 (Gieseking Ed., Springer, Berlin 1975) and Humic Substances II Hays et al. Ed., Wiley Interscience, John Wiley, New York (1989), as well as Humus Chemistry, Genesis Composition Reactions, author F. J. Stevenson, John Wiley & Sons, New York (1994).

Environmental samples in which humic acid may be present include but are not limited to soil, sediment, sludge, decomposing biological matter, archaeological remains, peat bogs, compost and water that are terrestrial or subterranean in origin. Engineered DNA polymerases of the present invention may be particularly useful for replication or amplification reactions such as PCR wherein the nucleic acid to be replicated or amplified is comprised within or has been exposed to such environmental samples. Uses include for example, analytical, cloning, diagnostic and detection reactions in the fields of agriculture, horticulture, forestry, forensics, biological research and in the identification of organism and sample compositions.

Isolation and Use of Humic Acid in the Present Invention

Humic acid is typically extracted from humus on the basis of its solubility in strong alkali and subsequent precipitation in strong acid (Swift, R. S. in "Methods of soil analysis. Part 3: Chemical methods", Sparks, D. L. (Ed.), Soil Sci. Soc. Am., Madison, 1996, pp. 1018-1020). The remaining solubilized material is a somewhat refined version of humic acid, referred to as fulvic acid. Soluble preparations of humic acids are also commercially available, especially as plant food supplements. Technical grade humic acid can be obtained for example from Sigma-Alrich Company Ltd, Gillingham, UK, product number 53680, CAS number 1415-93-6. As illustrated in Example 1 below, solutions of humic acid may be prepared and used to test candidate engineered DNA polymerases for resistance to humic acid. Candidate DNA polymerases may be tested in any replication or amplification reaction, for example, PCR. Preferably, candidate DNA polymerases are selected by directed evolution of DNA polymerases in the presence of humic acid as a selection pressure. Humic acid may be added to each compartment or microcapsule during compartmentalised self replication, for example, or in any other method of directed evolution. Addition of humic acid to each compartment can be used to select for DNA polymerases having activity under such conditions.

Resistance or an enhanced ability to process nucleic acid, is conveniently expressed in terms of humic acid concentration, which is found to inhibit the activity of the selected engineered DNA polymerase, compared to the concentration, which is found to inhibit the wild type DNA polymerase enzyme. Thus, the engineered DNA polymerases, selected by our invention may have 2×, 4×, 6×, 8×, 10×, 12×, 14×, 15×, 16×, 18×, 20×, 22×, 25×, 30×, or more resistance or enhanced ability to process nucleic acid, compared to the wild type DNA polymerase enzyme. Most preferably, the engineered DNA polymerases of the present invention have 16× or more fold enhanced ability to process nucleic acid when compared this way. The selected engineered DNA polymerases preferably have 50% or more, 60% or more, 70% or more, 80% or more, 90% or more, or even 100% activity at the concentration of the inhibitory factor.

Phenolic Compounds

Humic acid consists of a mixture of complex macromolecules having polymeric phenolic structures (Merck Index $13^{th}$ Edition).

The term "phenolic compounds" or polyphenols refers to a range of substances that possess an aromatic ring bearing one or more hydroxyl substitutions. Phenolic compounds are products of secondary metabolism in plants and are widespread throughout the plant kingdom. Major classes of plant phenolic compounds include simple phenols, phenolic acids, phenylacetic acids, courmarines, naphthoquinones, stilbenes/ anthraquinones, flavonoids/isoflavonoids and lignins (for more details see Harbone J B 1980, "Plant Phenolics in Encyclopedia of Plant Physiology, volume 8, pages 329-395, edited by Bell E A and Charlwood B V, published by Springer-Verlag, Berlin Heidelberg New York). The detection and extraction of phenolic compounds from soil or other biological samples is well known to those skilled in the art (Mahugo Santana et al Anal Bioanal Chem (2005) 382(1): 125-33, Shin et al J Biotechnol (2005) 119(1):36-43).

The term "phenolic acids" refers to acidic derivatives of phenol including but not limited to caffeic acid, vanillin, ferulic acid, gallic acid, ellagic acid and coumaric acid. Phenolic acids form a diverse group that includes two main categories: the hydroxybenzoic acids and the hydroxycinnamic acids (King and Young, J Am Diet Assoc. (1999) 99(2):213- 8). "Phytophenolic acids" refers to phenolic acids derived from plant material. Phenolic acids may occur in plants as esters or glycosides conjugated with other natural compounds such as flavonoids, alcohols, hydroxyfatty acids, sterols, and glucosides. Hydroxycinnamic acid compounds occur most frequently as simple esters with hydroxy carboxylic acids or glucose. Hydroxybenzoic acid compounds are present mainly in the form of glucosides. Methods for the extraction of phenolic acids from biological samples are discussed in Luthria and Mukhopadhyay (2006) J. Agric. Food Chem 54:41-47.

Polymerases

Polymerase enzymes are able to catalyse the production of new DNA or RNA from an existing DNA or RNA template—a process known as polymerisation. There are many different types of polymerases including DNA polymerases, RNA polymerases and reverse transcriptases. The methods described in the present application may be used to generate engineered polymerases including RNA polymerases, DNA polymerase or reverse transcriptases that are resistant to humic acid or to phenolic compounds.

RNA Polymerases

RNA polymerases (RNAP) catalyze the polymerisation of an RNA strand from a DNA template in the process of transcription. RNAP can initiate transcription at specific DNA sequences known as promoters. It then produces an RNA chain which is complementary to the DNA strand used as a template. The process of adding nucleotides to the RNA strand is known as elongation. In contrast to DNA polymerases, RNAP includes a helicase activity therefore no separate enzyme is needed to unwind DNA. However, RNAPs do work in association with a number of accessory factors. Such factors may control a variety of polymerase related processes such as the timing and specificity of gene expression (Kaiser et al Trends Biochem Sci. (1996) 21(9):325-6) or transcription-coupled repair (Lane T F, Cancer Biol Ther. (2004) 3(6): 528-33).

In eukaryotes the transcription of nucleus-encoded genes is performed by three distinct RNA polymerases termed, I, II and III (Archambault J et al; Microbiol Rev. (1993) 57(3): 703-24). RNA polymerase I is involved in the synthesis of ribosomal RNA, RNA polymerase II is involved in the synthesis of mRNA precursors and snRNA, and RNA polymerase III synthesises tRNA and other small RNAs. In bacteria the same enzyme catalyses the synthesis of three types of RNA: mRNA, rRNA and tRNA. The core enzyme has 5 subunits (two α subunits, (β, β$^1$ and ω) of which the β subunit catalyses the synthesis of RNA. A further discussion of the structure, function and regulation of other RNA polymerases in eukaryotes and prokaryotes is provided in Mooney et al Cell, (1999), Vol. 98:687-690 and Cramer P (2002) Curr Opin Struct Biol 12(1):89-97.

DNA Polymerases

Engineered DNA polymerases according to the present invention exhibit at least some resistance to humic acid or phenolic compounds DNA polymerase enzymes are naturally occurring intracellular enzymes, and are used by a cell to replicate nucleic acid strands. During the process of replication, a nucleotide sequence of a DNA strand is copied by complementary base-pairing into a complementary nucleic acid sequence. Each nucleotide in the DNA strand is recognised by an unpolymerised complementary nucleotide and requires that the two strands of the DNA helix be separated, at least transiently, so that the hydrogen bond donor and acceptor groups on each base become exposed for base-pairing. The appropriate incoming single nucleotides are thereby aligned for their enzyme-catalysed polymerization into a new nucleic acid chain.

Enzymes having DNA polymerase activity catalyze the formation of a bond between the 3' hydroxyl group at the growing end of a nucleic acid primer sequence and the 5' phosphate group of a nucleotide triphosphate. These nucleotide triphosphates are usually selected from deoxyadenosine triphosphate (A), deoxythymidine triphosphate (T), deoxycytidine triphosphate (C) and deoxyguanosine triphosphate (G). However, DNA polymerases may incorporate modified or altered versions of these nucleotides. The order in which the nucleotides are added is dictated by base pairing to a DNA template strand; such base pairing is accomplished through "canonical" hydrogen-bonding (hydrogen-bonding between A and T nucleotides and G and C nucleotides of opposing DNA strands), although non-canonical base pairing, such as G:U base pairing, is known in the art. See e.g., Adams et al., The Biochemistry of the Nucleic Acids 14-32 (11th ed. 1992).

The in-vitro use of enzymes having DNA polymerase activity has in recent years become more common in a variety of biochemical applications including cDNA synthesis and DNA sequencing reactions (see Sambrook et al., (2nd ed. Cold Spring Harbor Laboratory Press, 1989) hereby incorporated by reference herein), and amplification of nucleic acids by methods such as the polymerase chain reaction (PCR) (Mullis et al., U.S. Pat. Nos. 4,683,195, 4,683,202, and 4,800,159, hereby incorporated by reference herein) and RNA transcription-mediated amplification methods (e.g., Kacian et al., PCT Publication No. WO91/01384).

Methods such as PCR make use of cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37° C. to 42° C. (thermostable DNA polymerase enzymes) provides an advantage in cost and labor efficiency. Thermostable DNA polymerases have been discovered in a number of thermophilic organisms including, but not limited to *Thermus aquaticus*, *Thermus thermophilus*, and species of the *Bacillus*, *Thermococcus*, *Sulfolobus*, *Pyrococcus* genera. DNA polymerases can be purified directly from these thermophilic organisms. However, substantial increases in the yield of DNA polymerase can be obtained by first cloning the gene encoding the enzyme in a multicopy expression vector by recombinant DNA technology methods, inserting the vector into a host cell strain capable of expressing the enzyme, culturing the vector-containing host cells, then extracting the DNA polymerase from a host cell strain which has expressed the enzyme.

Preferably, the DNA polymerase of the present invention is a thermostable polymerase. A "thermostable" DNA polymerase as used here is a polymerase, which demonstrates significant resistance to thermal denaturation at elevated temperatures, typically above body temperature (37° C.). Preferably, such a temperature is in the range 42° C. to 160° C., more preferably, between 60 to 100° C., most preferably, above 90° C. Compared to a non-thermostable polymerase, the thermostable polymerase displays a significantly increased half-life (time of incubation at elevated temperature that results in 50% loss of activity). Preferably, the thermostable polymerase retains 30% or more of its activity after incubation at the elevated temperature, more preferably, 40%, 50%, 60%, 70% or 80% or more of its activity. Yet more preferably, the replicase retains 80% activity. Most preferably, the activity retained is 90%, 95% or more, even 100%. None-thermostable polymerases would exhibit little or no retention of activity after similar incubations at the elevated temperature.

The bacterial DNA polymerases that have been characterized to date have certain patterns of similarities and differences which has led some to divide these enzymes into two groups: those whose genes contain introns/inteins (Class B DNA polymerases), and those whose DNA polymerase genes are roughly similar to that of *E. coli* DNA polymerase I and do not contain introns (Class A DNA polymerases).

Several Class A and Class B thermostable DNA polymerases derived from thermophilic organisms have been cloned and expressed. Among the class A enzymes: Lawyer, et al., J. Biol. Chem. 264:6427-6437 (1989) and Gelfund et al, U.S. Pat. No. 5,079,352, report the cloning and expression of a full length thermostable DNA polymerase derived from *Thermus aquaticus* (Taq). Lawyer et al., in PCR Methods and Applications, 2:275-287 (1993), and Barnes, PCT Publication No. WO92/06188 (1992), disclose the cloning and expression of truncated versions of the same DNA polymerase, while Sullivan, EPO Publication No. 0482714A1 (1992), reports cloning a mutated version of the Taq DNA polymerase. Asakura et al., J. Ferment. Bioeng. (Japan), 74:265-269 (1993) have reportedly cloned and expressed a DNA polymerase from *Thermus thermophilus*. Gelfund et al., PCT Publication No. WO92/06202 (1992), have disclosed a purified thermostable DNA polymerase from *Thermosipho africanus*. A thermostable DNA polymerase from *Thermus flavus* is reported by Akhmetzjanov and Vakhitov, Nucleic Acids Res., 20:5839 (1992). Uemori et al., J. Biochem. 113: 401-410 (1993) and EPO Publication No. 0517418A2 (1992) have reported cloning and expressing a DNA polymerase from the thermophilic bacterium *Bacillus caldotenax*. Ishino-et al., Japanese Patent Application No. HEI 4[1992]-131400 (publication date Nov. 19, 1993) report cloning a DNA polymerase from *Bacillus stearothermophilus*. Among the Class B enzymes: A recombinant thermostable DNA polymerase from *Thermococcus litoralis* is reported by Comb et al., EPO Publication No. 0 455 430 A3 (1991), Comb et al., EPO Publication No. 0547920A2 (1993), and Perler et al., Proc. Natl. Acad. Sci. (USA), 89:5577-5581 (1992). A cloned thermostable DNA polymerase from *Sulfolobus solofatarius* is disclosed in Pisani et al., Nucleic Acids Res. 20:2711-2716 (1992) and in PCT Publication WO93/25691 (1993). The thermostable enzyme of *Pyrococcus furiosus* is disclosed in Uemori et al., Nucleic Acids Res., 21:259-265 (1993), while a recombinant DNA polymerase is derived from *Pyrococcus* sp. as disclosed in Comb et al., EPO Publication No. 0547359A1 (1993).

Many thermostable DNA polymerases possess activities additional to a DNA polymerase activity; these may include a 5'-3' exonuclease activity and/or a 3'-5' exonuclease activity. The activities of 5'-3' and 3'-5' exonucleases are well known to those of ordinary skill in the art. The 3'-5' exonuclease activity improves the accuracy of the newly-synthesized strand by removing incorrect bases that may have been incorporated; DNA polymerases in which such activity is low or absent, reportedly including Taq DNA polymerase, (see Lawyer et al., J. Biol. Chem. 264:6427-6437), have elevated error rates in the incorporation of nucleotide residues into the primer extension strand. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is a desired characteristic of a thermostable DNA polymerase used for such purposes.

By contrast, the 5'-3' exonuclease activity often present in DNA polymerase enzymes is often undesired in a particular application since it may digest nucleic acids, including primers, that have an unprotected 5' end. Thus, a thermostable DNA polymerase with an attenuated 5'-3' exonuclease activity, or in which such activity is absent, is also a desired characteristic of an enzyme for biochemical applications. Various DNA polymerase enzymes have been described where a modification has been introduced in a DNA polymerase, which accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, supra, and Gelfund et al., U.S. Pat. No. 5,079,352 have produced 5'-3' exonuclease-deficient recombinant Taq DNA polymerases. Ishino et al., EPO Publication No. 0517418A2, have produced a 5'-3' exonuclease-deficient DNA polymerase derived from *Bacillus caldotenax*. On the other hand, polymerases lacking the 5'-3' exonuclease domain often have reduced processivity.

Polymerase Chain Reaction and Other Amplification Techniques

Amplification

The methods for generation of engineered DNA polymerases in our invention involve the templated amplification of desired nucleic acids. "Amplification" refers to the increase in the number of copies of a particular nucleic acid fragment (or a portion of this) resulting either from an enzymatic chain reaction (such as a polymerase chain reaction), or from the replication of all or part of the vector into which it has been cloned. Preferably, the amplification according to our invention is an exponential amplification, as exhibited by for example the polymerase chain reaction.

Many target and signal amplification methods have been described in the literature, for example, general reviews of these methods in Landegren, U., et al., Science 242:229-237 (1988) and Lewis, R., Genetic Engineering News 10:1, 54-55 (1990).

Polymerase Chain Reaction (PCR)

PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The primer may be the same chemically, or different from, the extended sequence (for example, mammalian DNA polymerase is known to extend a DNA sequence from an RNA primer). The DNA is copied by primer extension to make a second copy of both strands. By repeating the cycle of heat denaturation, primer hybridization and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours.

The polymerase chain reaction may be used in the selection methods of our invention as follows. For example, PCR may be used to select for variants of Taq polymerase having polymerase activity. As described in further detail above, a library of nucleic acids each encoding a DNA polymerase or a variant of the DNA polymerase, for example, Taq polymerase, is generated and subdivided into compartments. Each compartment comprises substantially one member of the library together with the DNA polymerase or variant encoded by that member.

The DNA polymerase or variant may be expressed in vivo within a transformed bacterium or any other suitable expression host, for example yeast or insect or mammalian cells, and the expression host encapsulated within a compartment. Heat or other suitable means is applied to disrupt the host and to release the polymerase variant and its encoding nucleic acid within the compartment. In the case of a bacterial host, timed expression of a lytic protein, for example protein E from ΦX174, or use of an inducible λ lysogen, may be employed for disrupting the bacterium.

It will be clear that the DNA polymerase need not be a heterologous protein expressed in that host (e.g., a plasmid), but may be expressed from a gene forming part of the host genome. Thus, the polymerase may be for example an endogenous or native bacterial polymerase. Thus, the methods of selection according to our invention may be employed for the direct functional cloning of DNA polymerases from diverse (and uncultured) microbial populations.

Alternatively, the nucleic acid library may be compartmentalised together with components of an in vitro transcription/translation system (as described in further detail in this document), and the polymerase variant expressed in vitro within the compartment.

Each compartment also comprises humic acid. It is desirable that humic acid is added at a concentration sufficient to provide a selection pressure, so that humic acid resistant DNA polymerases may be selected for. Importantly, the concentration of humic acid should not be so great that total inhibition of the polymerase activity occurs and accordingly no humic acid resistant polymerases can be selected.

Each compartment also comprises components for a PCR reaction, for example, nucleotide triphosphates (dNTPs), buffer, magnesium, and oligonucleotide primers. The oligonucleotide primers may have sequences corresponding to sequences flanking the polymerase gene (i.e., within the genomic or vector DNA) or to sequences within the polymerase gene. PCR thermal cycling is then initiated to allow any polymerase variant having polymerase activity to amplify the nucleic acid sequence.

Active polymerases will amplify their corresponding nucleic acid sequences, while nucleic acid sequences encoding weakly active or inactive polymerases will be weakly replicated or not be replicated at all. In general, the final copy number of each member of the nucleic acid library will be expected to be proportional to the level of activity of the polymerase variant encoded by it. Nucleic acids encoding active polymerases will be over-represented, and nucleic acids encoding inactive or weakly active polymerases will be under-represented. The resulting amplified sequences may then be cloned and sequenced, etc, and replication ability of each member assayed.

Reverse Transcriptase-PCR

RT-PCR is used to amplify RNA targets. In this process, the reverse transcriptase enzyme is used to convert RNA to complementary DNA (cDNA), which can then be amplified using PCR. This method has proven useful for the detection of RNA viruses.

The methods of our invention may employ RT-PCR and the engineered DNA polymerases of the present invention may be used in RT-PCR. The pool of nucleic acids encoding the DNA polymerase or its variants may be provided in the form of an RNA library. This library could be generated in vivo in bacteria, mammalian cells, yeast etc, which are compartmentalised, or by in-vitro transcription of compartmentalised DNA. The RNA could encode a co-compartmentalised DNA polymerase that has been expressed in vivo (and released in emulsion along with the RNA by means disclosed below) or in vitro. Other components necessary for amplification (polymerase and/or reverse transcriptase, dNTPs, primers) are also compartmentalised. Under the humic acid selection pressure, the cDNA product of the reverse transcription reaction serves as a template for PCR amplification.

Other Amplification Techniques

Alternative amplification technology may be exploited in the present invention. For example, rolling circle amplification (Lizardi et al., (1998) Nat Genet. 19:225) is an amplification technology available commercially (RCAT™) which is driven by DNA polymerase and can replicate circular oligonucleotide probes with either linear or geometric kinetics under isothermal conditions.

In the presence of two suitably designed primers, a geometric amplification occurs via DNA strand displacement and hyperbranching to generate $10^{12}$ or more copies of each circle in 1 hour.

If a single primer is used, RCAT generates in a few minutes a linear chain of thousands of tandemly linked DNA copies of a target covalently linked to that target.

A further technique, strand displacement amplification (SDA; Walker et al., (1992) PNAS (USA) 80:392) begins with a specifically defined sequence unique to a specific target. But unlike other techniques which rely on thermal cycling, SDA is an isothermal process that utilizes a series of primers, DNA polymerase and a restriction enzyme to exponentially amplify the unique nucleic acid sequence.

SDA comprises both a target generation phase and an exponential amplification phase.

In target generation, double-stranded DNA is heat denatured creating two single-stranded copies. A series of specially manufactured primers combine with DNA polymerase (amplification primers for copying the base sequence and bumper primers for displacing the newly created strands) to form altered targets capable of exponential amplification.

The exponential amplification process begins with altered targets (single-stranded partial DNA strands with restricted enzyme recognition sites) from the target generation phase.

An amplification primer is bound to each strand at its complimentary DNA sequence. DNA polymerase then uses the primer to identify a location to extend the primer from its 3' end, using the altered target as a template for adding individual nucleotides. The extended primer thus forms a double-stranded DNA segment containing a complete restriction enzyme recognition site at each end.

A restriction enzyme is then bound to the double stranded DNA segment at its recognition site. The restriction enzyme dissociates from the recognition site after having cleaved only one strand of the double-sided segment, forming a nick. DNA polymerase recognizes the nick and extends the strand from the site, displacing the previously created strand. The recognition site is thus repeatedly nicked and restored by the restriction enzyme and DNA polymerase with continuous displacement of DNA strands containing the target segment.

Each displaced strand is then available to anneal with amplification primers as above. The process continues with repeated nicking, extension and displacement of new DNA strands, resulting in exponential amplification of the original DNA target.

Directed Evolution

In a preferred embodiment the present invention provides a method for the generation of an engineered DNA polymerase which comprises the steps of:
 (a) providing a pool of nucleic acids comprising members each encoding a DNA polymerase or a variant of the DNA polymerase;
 (b) providing humic acid;
 (c) subdividing the pool of nucleic acids into compartments, such that each compartment comprises substantially a nucleic acid member of the pool together with the DNA polymerase or variant encoded by the nucleic acid member, and humic acid;
 (d) allowing processing of the nucleic acid member to occur; and
 (e) detecting processing of the nucleic acid member by the DNA polymerase; and optionally repeating the series of steps (a) to (f) one or more times.

The techniques of directed evolution and compartmentalised self replication are detailed in GB 97143002 and GB 98063936 and GB 01275643, in the name of the present inventors. These documents are herein incorporated by reference.

In its simplest form CSR involves the segregation of genes coding for and directing the production of DNA polymerases within discrete, spatially separated, aqueous compartments of a novel heat-stable water-in-oil emulsion. Provided with nucleotide triphosphates and appropriate flanking primers, polymerases replicate only their own genes. Consequently, only genes encoding active polymerases are replicated, while inactive variants that cannot copy their genes disappear from the gene pool. By analogy to biological systems, among differentially adapted variants, the most active (the fittest) produce the most "offspring", hence directly correlating post-selection copy number with enzymatic turn-over.

Thus, by exposing repertoires of DNA polymerase genes (diversified through targeted or random mutation) to self-amplification and by altering the conditions under which self-amplification can occur, the system can be used for the isolation and engineering of polymerases with enhanced resistance to humic acid.

Encapsulation of PCRs has been described previously for lipid vesicles (Oberholzer, T., Albrizio, M. & Luisi, P. L. (1995) *Chem. Biol.* 2, 677-82 and fixed cells and tissues (Haase, A. T., Retzel, E. F. & Staskus, K. A. (1990) *Proc. Natl. Acad. Sci. USA* 87, 4971-5; Embleton, M. J., Gorochov, G., Jones, P. T. & Winter, G. (1992) *Nucleic Acids*) but with low efficiencies.

Principles Underlying CST Technology
Microcapsules

The compartments or "microcapsules" used according to the method of the invention require appropriate physical properties to allow the working of the invention.

First, to ensure that the nucleic acids and gene products may not diffuse between microcapsules, the contents of each microcapsule must be isolated from the contents of the surrounding microcapsules, so that there is no or little exchange of the nucleic acids and gene products between the microcapsules over the timescale of the experiment.

Second, the method of the present invention requires that there are only a limited number of nucleic acids per microcapsule. This ensures that the gene product of an individual nucleic acid will be isolated from other nucleic acids. Thus, coupling between nucleic acid and gene product will be highly specific. The enrichment factor is greatest with on average one or fewer nucleic acids per microcapsule, the linkage between nucleic acid and the activity of the encoded gene product being as tight as is possible, since the gene product of an individual nucleic acid will be isolated from the products of all other nucleic acids. However, even if the theoretically optimal situation of, on average, a single nucleic acid or less per microcapsule is not used, a ratio of 5, 10, 50, 100 or 1000 or more nucleic acids per microcapsule may prove beneficial in sorting a large library. Subsequent rounds of sorting, including renewed encapsulation with differing nucleic acid distribution, will permit more stringent sorting of the nucleic acids. Preferably, there is a single nucleic acid, or fewer, per microcapsule.

Third, the formation and the composition of the microcapsules must not abolish the function of the machinery the expression of the nucleic acids and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™80; ICI) and polyoxyethylenesorbitan monooleate (Tween™80; ICD and Triton-X-100.

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the nucleic acids and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of nucleic acids or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

Expression within Microcapsules

The processes of expression must occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 μm, more preferably less than $6.5 \times 10^{-17}$ m$^3$ (5 μm), more preferably about $4.2 \times 10^{-18}$ m$^3$ (2 μm) and ideally about $9 \times 10^{-18}$ m$^3$ (2.6 μm).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qb replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^{-16}$ m$^3$ (corresponding to a sphere of diameter 10 um).

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules must be contained within a microcapsule of volume $4.17 \times 10^{-19}$ litres ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 100 nm.

Therefore, the microcapsule volume is preferably of the order of between $5.2 \times 10^{-22}$ m$^3$ and $5.2 \times 10^{-16}$ m$^3$ corresponding to a sphere of diameter between 0.1 um and 10 um, more preferably of between about $5.2 \times 10^{-19}$ m$^3$ and $6.5 \times 10^{-17}$ m$^3$ (1 um and 5 um). Sphere diameters of about 2.6 um are most advantageous.

It is no coincidence that the preferred dimensions of the compartments (droplets of 2.6 um mean diameter) closely resemble those of bacteria, for example, *Escherichia* are 1.1-1.5×2.0-6.0 um rods and *Azotobacter* are 1.5-2.0 μm diameter ovoid cells. In its simplest form, Darwinian evolution is based on a 'one genotype one phenotype' mechanism. The concentration of a single compartmentalised gene, or genome, drops from 0.4 nM in a compartment of 2 um diameter, to 25 μM in a compartment of 5 um diameter. The prokaryotic transcription/translation machinery has evolved to operate in compartments of ~1-2 um diameter, where single genes are at approximately nanomolar concentrations. A single gene, in a compartment of 2.6 um diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the nucleic acid itself. The volume of the microcapsule should thus be selected bearing in mind not only the requirements for transcription and translation of the nucleic acid/nucleic acid, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given nucleic acid/nucleic acid library, since the ultimately limiting factor will be the size of the microcapsule and thus the number of microcapsules possible per unit volume.

The size of the microcapsules is selected not only having regard to the requirements of the transcription/translation system, but also those of the selection system employed for the nucleic acid/nucleic acid construct. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "nucleic acid" in accordance with the present invention is as described above. Preferably, a nucleic acid is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like.

The nucleic acid portion of the nucleic acid may comprise suitable regulatory sequences, such as those required for efficient expression of the gene product, for example promoters, enhancers, translational initiation sequences, polyadenylation sequences, splice sites and the like.

Product Selection

A ligand or substrate can be connected to the nucleic acid by a variety of means that will be apparent to those skilled in the art (see, for example, Hermanson, 1996). Any tag will suffice that allows for the subsequent selection of the nucleic acid. Sorting can be by any method which allows the preferential separation, amplification or survival of the tagged nucleic acid. Examples include selection by binding (including techniques based on magnetic separation, for example using Dynabeads™), and by resistance to degradation (for example by nucleases, including restriction endonucleases).

One way in which the nucleic acid molecule may be linked to a ligand or substrate is through biotinylation. This can be done by PCR amplification with a 5'-biotinylation primer such that the biotin and nucleic acid are covalently linked.

The ligand or substrate to be selected can be attached to the modified nucleic acid by a variety of means that will be apparent to those of skill in the art. A biotinylated nucleic acid may be coupled to a polystyrene microbead (0.035 to 0.2 um in diameter) that is coated with avidin or streptavidin, that will therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the alpha-amino group of lysines or through a non-covalent interaction such as biotin-avidin. The substrate may be present in a form unlinked to the nucleic acid but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" could then be activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

When all reactions are stopped and the microcapsules are combined, the nucleic acids encoding active enzymes can be enriched using an antibody or other molecule which binds, or reacts specifically with the "tag". Although both substrates and product have the molecular tag, only the nucleic acids encoding active gene product will co-purify.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired nucleic acids from pools (libraries or repertoires) of nucleic acids which contain the desired nucleic acid. Selecting is used to refer to the process (including the sorting process) of isolating an entity according to a particular property thereof.

Microcapsules/Sorting

In addition to the nucleic acids described above, the microcapsules according to the invention will comprise further components required for the sorting process to take place. Other components of the system will for example comprise those necessary for transcription and/or translation of the nucleic acid. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of nucleic acids for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

Microcapsule Identification

Microcapsules may be identified by virtue of a change induced by the desired gene product which either occurs or manifests itself at the surface of the microcapsule or is detectable from the outside as described in the section "Microcapsule Sorting". This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the nucleic acid. A similar procedure has been described previously for the rapid sorting of cells (Keij et al., 1994). Modification of the nucleic acid may result, for example, from coupling a molecular "tag", caged by a photolabile protecting group to the nucleic acids: bombardment with photons of an appropriate wavelength leads to the removal of the cage. Afterwards, all microcapsules are combined and the nucleic acids pooled together in one environment. Nucleic acids encoding gene products exhibiting the desired activity can be selected by affinity purification using a molecule that specifically binds to, or reacts specifically with, the "tag".

Multi Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each nucleic acid of a nucleic acid library may take place in a first microcapsule. Each gene product is then linked to the nucleic acid which encoded it (which resides in the same microcapsule). The microcapsules are then broken, and the nucleic acids attached to their respective gene products optionally purified. Alternatively, nucleic acids can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified nucleic acid attached to its gene product is put into a second microcapsule containing components of the reaction to be selected. This reaction is then initiated. After completion of the reactions, the microcapsules are again broken and the modified nucleic acids are selected. In the case of complicated multi-step reactions in which many individual components and reaction steps are involved, one or more intervening steps may be performed between the initial step of creation and linking of gene product to nucleic acid, and the final step of generating the selectable change in the nucleic acid.

Libraries of Nucleic Acid Sequences

Herein, the terms "library", "repertoire" and "pool" are used according to their ordinary signification in the art, such that a library of nucleic acids encodes a repertoire of gene products. Initial selection of a nucleic acid/nucleic acid from a nucleic acid library (for example a mutant taq library) according to the present invention will in most cases require the screening of a large number of variant nucleic acids. Libraries of nucleic acids can be created in a variety of different ways, including the following.

Pools of naturally occurring nucleic acids can be cloned from genomic DNA or cDNA (Sambrook et al., 1989); for example, mutant Taq libraries or other DNA polymerase libraries, made by PCR amplification repertoires of taq or other DNA polymerase genes have proved very effective sources of DNA polymerase fragments.

Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a nucleic acid or pool of nucleic acids 'randomly' by a variety of techniques in vivo, including; using 'mutator strains', of bacteria such as *E. coli* mutD5 (Liao et al., 1986; Yamagishi et al., 1990; Low et al., 1996). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases. Error-prone PCR introduces random copying errors by imposing imperfect, and thus mutagenic, or "sloppy" reaction conditions (for example by adding $Mn^{2+}$ or $Mg^{2+}$ to the reaction mixture (Cadwell and Joyce, 1991, PCR Meth. Appl. 2:28-33; Leung et al., 1989, Technique 1:11-13). This method has proven useful for generation of randomised libraries of nucleotide sequences. According to the method of the invention, the term 'random' may be in terms of random positions with random repertoire of amino acids at those positions or it may be selected (predetermined) positions with random repertoire of amino acids at those selected positions.

Further diversification can be introduced by using homologous recombination either in vivo (see Kowalczykowski et al., 1994 or in vitro (Stemmer, 1994a; Stemmer, 1994b)). An example of an in vitro homologous recombination technique to generate gene diversity is gene shuffling.

Gene shuffling involves random fragmentation of several mutant DNAs followed by their reassembly by PCR into full length molecules (Smith, Nature, 370: 324 [1994]). Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, Nature, 370: 398 [1994]; Stemmer, Proc. Natl. Acad. Sci. USA, 91: 10747 [1994]; Crameri et al., Nat. Biotech., 14: 315 [1996]; Zhang et al., Proc. Natl. Acad. Sci. USA, 94: 4504 [1997]; and Crameri et al., Nat. Biotech., 15: 436 [1997]).

A modification of gene shuffling, the Staggered Extension Protocol (StEP) has been described (WO 98/42832; Shao et al., 1998; Zhao et al., 1997; Zhao et al., 1998). StEP involves priming template polynucleotides with random or flanking primers. Extended primers are reassembled in extremely fast cycles of PCR, generating successively longer and longer extension products. In each cycle the primers/extension products can anneal to different templates based on sequence complementarity. The template switching between different sequences creates "recombination cassettes". The process is continued until full-length genes are created.

A modification of the StEP technology has also been described (U.S. Pat. No. 5,965,408). Like StEP, random primers are annealed to a target(s) to be shuffled. The random primers are extended until stopped by "roadblocks" such as purine dimers. The premature termination is facilitated by blocking the polymerase with adducts associated with the template. Fragments are isolated and used in a separate PCR reaction to create longer overlapping fragments.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of DNA polymerase homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Directed evolution techniques for detection and selection of desired DNA polymerase activity have already been described.

Vectors and Host Cells

Suitable vectors and host cells may be used to host nucleic acid encoding candidate DNA polymerases, or libraries thereof, or engineered DNA polymerases of the present invention. Host cells and vectors may also be used to express and isolate candidate DNA polymerase polypeptides or engineered DNA polymerases of the present invention. Suitable host cells may also be used to isolate wild type DNA polymerase genes and alternatively or additionally, to express wild type DNA polymerase polypeptides for use in the methods of the present invention.

Vectors

Expression vectors may be constructed from a starting vector such as a commercially available vector. Preferred vectors are those which are compatible with bacterial, insect, and mammalian host cells. Such vectors include, inter alia, pCRH, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), pASK75, and mammalian, yeast or virus vectors such as a baculovirus expression system (pBacPAK plasmid derivatives, Clontech, Palo Alto, Calif.).

Vectors may also include a transcription regulatory element (a promoter) operably linked to the DNA polymerase sequence. The promoter may optionally contain operator portions and/or ribosome binding sites. Non-limiting examples of bacterial promoters compatible with E. coli include: trc promoter, alpha-lactamase (penicillinase) promoter; lactose promoter; tryptophan (trp) promoter; arabinose BAD operon promoter; lambda-derived PI promoter and N gene ribosome binding site; and the hybrid tac promoter derived from sequences of the trp and lac UV5 promoters.

After the vector has been constructed and a nucleic acid molecule encoding a DNA polymerase polypeptide has been inserted into the proper site of the vector, the completed vector may be inserted into a suitable host cell for amplification and/or polypeptide expression. The transformation of an expression vector for a DNA polymerase polypeptide into a selected host cell may be accomplished by well known methods including methods such as transfection, infection, calcium chloride, electroporation, microinjection, lipofection, DEAF-dextran method, or other known techniques. The method selected will in part be a function of the type of host cell to be used. These methods and other suitable methods are well known to the skilled artisan, and are set forth, for example, in Sambrook et al., supra.

Host Cells

By "host cell" or "recombinantly engineered cell" is meant a cell, which contains a vector and supports the replication and/or expression of the expression vector. Host cells may be prokaryotic host cells (such as E. coli) or eukaryotic host cells (such as a yeast, insect, or vertebrate cell). The host cell, when cultured under appropriate conditions, synthesizes a DNA polymerase polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Of particular interest as host cells are bacterial cells. For example, the various strains of E. coli (e.g., HB101, DH5α, DH10, and MC1061) are well known as host cells in the field of biotechnology. Various strains of B. subtilis, Pseudomonas spp., other Bacillus spp., Streptomyces spp., and the like may also be employed in methods used in the present invention.

Host cells may be used to express heterologous candidate or engineered DNA polymerases of the present invention. As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced DNA polymerases or derived peptides and polypeptides.

EXAMPLES

Example 1

Libraries of Polymerase Chimeras

Libraries of chimeric polymerase gene variants were constructed using the Step shuffling PCR technique (Zhao et al., (1998) *Nature Biotechnol.* 16, 258-261).

For a first library 3T: *Thermus aquaticus* (Taq) wild type and T8 (a previously selected 11 fold more thermostable Taq variant (Ghadessy et al. Proc Natl Acad Sci U S A. 2001 Apr. 10; 98(8):4552-7), *Thermus thermophilus* (Tth) and *Thermus flavus* (Tfl) polymerase genes were amplified from genomic DNA and cloned into pASK75 (Skerra 1994) and tested for activity. These genes were shuffled using Step, then recloned into pASK75 and transformed into *E. coli* TG1 giving library 3T.

For a second more diverse library 8T, we amplified the Pol I genes from the genomic DNA of *Thermus brockianus, Thermus filiformis, Thermus scotoductus* and *Thermus oshimai* by PCR and cloned them into the pAsk75 vector.

T8 was then generated by Step as above including the Pol I genes of *Thermus thermophilus, Thermus aquaticus, Thermus flavus, Thermus brockianus, Thermus filiformis, Thermus scotoductus* and *Thermus oshimai* as well as *Deinococcus radiodurans* (a radiation resistant bacterium) which had previously been cloned into pAsk75 in our laboratory.

The library size was scored by dilution assays and determining the ratio of clones containing insert using PCR screening and was approximately $1 \times 10^8$ in both cases. A diagnostic restriction digest of 20 clones produced 20 unique restriction patterns, indicating that the library was diverse.

Subsequent sequencing of selected chimeras showed an average of 4 to 6 crossovers per gene.

Example 2

Production of Humic Acid

A sample of peat soil was broken into small pieces and water was added. The sample was then heated to 50° C. for 1 hour to aid solubilisation.

The resulting samples were spun down at 13000 rpm for 30 minutes and the water phase was recovered. The volume was then reduced 10 fold by using a concentrator.

The inhibitory activity of the resulting humic acid was tested by doing a 30 cycle PCR (94° C. 10 min), then 30 cycles of 94° C. 30 s, 50° C. 30 s, 72° C. 1 min then 65° C. 10 min in the presence of a two fold dilution series of humic acid from 60% humic acid to 0.03% (12 points). The PCR (1×SuperTaq buffer, 0.2 mM dNTP, 1 µM primers (AAA AAT CTA GAT AAC GAG GGC AA (SEQ ID NO: 11) and ACC ACC GAA CTG CGG GTG ACG CCA AGC G (SEQ ID NO: 12)), 1 µl SuperTaq, 2.5 µl of an overnight growth of *E. coli* cells and 0.01 µl of pAsk75 as template (100 µm stock), water and humic acid as required) was performed in the presence of *E. coli* cell debris as it is known that DNA and protein counteract to an extent the inhibitor effect that humic acid has on polymerases.

The humic acid solution was found to totally inhibit the PCR a concentration of 5% and above.

Example 3

Selection of Humic Acid Resistant Clones

CSR emulsification and selection was performed on the StEP Taq, Tth and Tfl library essentially as described (Ghadessy et al. 2001), but with the addition of humic acid to the water phase of the emulsion as the source of selective pressure. The highest amount of humic acid which produced a positive selection was 20%.

The primers used were (5'-GTA AAA CGA CGG CCA GTA CCA CCG AAC TGC GGG TGA CGC CAA GCG-3' (SEQ ID NO: 13), and 5'-CAG GAA ACA GCT ATG ACA AAA ATC TAG ATA ACG AGG GCA A-3'(SEQ ID NO: 14).

The aqueous phase was ether extracted, PCR purified (Qiagen, Chatsworth, Calif.) with an additional 35% GnHCl, digested with DpnI to remove methylated plasmid DNA, treated with ExoSAP (USB) to remove residual primers, reamplified with outnested primers (CAG GAA ACA GCT ATG AC (SEQ ID NO: 15) and GTA AAA CGA CGG CCA GT) (SEQ ID NO: 16)), recloned and transformed into *E. coli* as above.

The resultant clones were screened and ranked in order using a PCR assay. Briefly, 2.5 µl of induced cells were added to 20 µl of PCR mix ((1×SuperTaq buffer, 0.2 mM dNTP, 1 µM, 0.01 µl of pAsk75 (100 µM stock), water and humic acid as required) with the relevant primers (AAA AAT CTA GAT AAC GAG GGC AA (SEQ ID NO: 11) and ACC ACC GAA CTG CGG GTG ACG CCA AGC G) (SEQ ID NO: 12)). 6 Plates were screened at varying concentrations of humic acid (10%, 5%) and a total of 14 polymerases were isolated that worked in PCR under conditions were the WT did not (i.e. 5 or 10% humic acid): P1H2, P2E2, P3D5, P4D10, P4F12, P5E1, P5H2, P6A9, P6A10, P6C10, P6D1, P6F3, P6F4.

Example 4

Ranking of Selected Clones

Polymerase clones: P1H2, P2E2, P3D5, P4D10, P4F8, P4F12, P5E1, P5H2, P6A9, P6A10, P6C10, P6D1, P6F3 were streaked on selective agar plates and grown overnight at 37° C., diluted 1/100 into 2×TY/Amp incubated at 37° C. until O.D$_{595}$=0.5 (ca. 2 hours). Anhydrotetracycline was added to a final concentration of 0.04 µg/ml and cultures were induced for 4 hours at 37° C., shaking. Cells were spun down, supernatant was discarded and cell pellet resuspended in ¼ volume of 1× Taq buffer followed by incubation at 85° C. for 10 min. Lysate was cleared by centrifugation. Polymerases were normalized and ranked for activity in PCR essentially as in Ghadessy et al 2001 using PCR program ((94° C. 1 min, 30×(94° C. 30 sec, 50° C. 30 sec, 72° C. 1 min), 65° C. for 2 min) using primers 1: 5'-ACC ACC GAA CTG CGG GTG ACG CCA AG-3' (SEQ ID NO: 17) and 2: 5'-GGG TAC GTG GAG ACC CTC TTC GGC C-3' (SEQ ID NO: 18) and 10 ng of pASK-Taq vector as template. Resistance to humic acid inhibition was determined using serial dilution of peat extract humic acid (HuAc P) (see above) and commercially available humic acid (Fluka, product code: 53680; Lot: 1102067 34505220) (HuAc F (dissolved in 1× Taq buffer to saturation (i.e. limit orf solubility)) (Table 1).

TABLE 1

Activity in humic acid from two different sources

| Polymerase | activity | f$^a$ | Activity in HuAc P 1/10 | f$_{HuAcP}$$^b$ | Activity in HuAc F 1/50 | f$_{HuAcF}$$^c$ | f$_{HuAcP}$/f$_{HuAcF}$$^d$ |
|---|---|---|---|---|---|---|---|
| P2E2 | 1/128 | 4 | 1/16 | 0.25 | 1/64 | 0.03125 | 8 |
| P1H2 | 1/64 | 2 | 1/8 | 1 | 1/32 | 0.25 | 4 |
| P6A10 | 1/64 | 2 | 1/16 | 0.5 | 1/32 | 0.25 | 2 |
| P3D5 | 1/8 | 0.25 | 1/32 | 2 | 1/128 | 0.5 | 4 |
| P4D10 | 1/128 | 4 | 1/2 | 2 | 1/16 | 0.25 | 8 |
| P4F8 | 1/32 | 1 | 1/32 | 0.5 | 1/64 | 0.25 | 2 |
| P5H2 | 1/16 | 0.5 | 1/16 | 2 | 1/64 | 0.5 | 4 |
| P6A9 | 1/16 | 0.5 | 1/16 | 2 | 1/64 | 0.5 | 4 |
| P4F12 (Hu1) | 1/32 | 1 | 1/4 | 4 | 1/8 | 2 | 2 |
| P5E1 | 1/64 | 2 | 1/8 | 1 | 1/16 | 0.5 | 2 |
| P6C10 | 1/32 | 1 | 1/8 | 2 | 1/32 | 0.5 | 4 |
| P6D1 | 1/32 | 1 | 1/16 | 1 | 1/64 | 0.25 | 4 |
| P6F3 | 1/8 | 0.25 | 1/8 | 8 | 1/32 | 2 | 4 |
| Taqwt | 1/32 | 1 | 1/16 | 1 | 1/16 | 1 | 1 |

$^a$f: rel. activity vs Taqwt
$^b$f$_{HuAcP}$: rel. activity vs Taqwt in HuAc extracted from peat (HuAc P)
$^c$f$_{HuAcF}$: rel. activity vs Taqwt in HuAc from Fluka (HuAc F)
$^d$f$_{HuAcP}$/f$_{HuAcF}$: rel. activity in HuAc P vs HuAc F Clones show universally higher resistance to the inhibitory effects of HuAc P for which they were selected. P4F12 (Hu1) and P6F3 display the highest level of resistance (f$_{HuAcp}$) retaining activity at 4-resp. 8-fold the concentration of HuAc P at which Taqwt is completely inhibited in PCR. Resistance to HuAc F is low or absent. Only P4F12 (Hu1) and P6F3 display an increased resistance (2×) compared to wtTaq to commercially available humic acid (HuAc F).

This reflects the selection of polymerases for resistance to HuAc P and not HuAcF. The relative activity in HuAc P vs HuAc F (f$_{HuAcF}$/f$_{HuAcF}$) for Taqwt is 1, while most of the selected clones display a f$_{HuAcP}$/f$_{HuAcF}$ 2-8. HuAc P and HuAC F are clearly distinct and reflect the heterogenous nature of humic substances. Future selections may alternate between different humic acid preparations to ensure a general resistance to humic acids, although P4F12 (Hu1) and P6F3 already display a low level of general resistance.

Example 5

Selection of a Polymerase Resistant to Inhibition by Soil

Using standard CSR selection as described (Ghadessy et al., 2001), three polymerases were selected, which show an increased resistance towards soil inhibition compared to the wildtype *Thermus aquaticus* polymerase. The clones were selected after two rounds of CSR.

The soil sample used in the experiments was collected in Cambridge and showed a slightly alkaline pH.

For the first round of CSR an aliquot of the soil sample was used to set up a soil slurry in 1× Supertaq buffer, which was then added to the reaction as inhibitory reagent. In a control reaction with Supertaq polymerase, the first product was observable at a concentration of 0.3% of the soil slurry. The first round of CSR was then carried out in the presence of 2.5% soil slurry.

For the second round an aliquot of the soil sample was transferred into 1× Supertaq buffer and this soil slurry was then incubated for 2 hours at 50° C., followed by 20 minutes at 90° C. The extract was then centrifuged at 8.000 rpm for 10 minutes and the supernatant was kept as inhibitory solution (−20° C.).

The inhibitory concentration was then determined using Supertaq polymerase. The polymerase starts to get inhibited at around 3%, with an almost complete inhibition at 6% concentration. For the second round of CSR the inhibitory concentration was set to 5%.

In the presence of the inhibitor the resulting clones soil3, soil4 and soil5 appear to be twice (soil3, soil4) respectively three times (soil5) more active than the wildtype *Thermus aquaticus* polymerase.

All polymerases were stored in glycerol in liquid nitrogen.

The invention claimed is:

1. An engineered polymerase consisting of the amino acid sequence of SEQ ID NO: 2 and exhibiting at least a two-fold enhanced ability compared to the ability of the wild type *Thermus aquaticus* polymerase to process nucleic acid in the presence of humic acid at a concentration between 5 and 20%.

2. An engineered polymerase consisting of the amino acid sequence of SEQ ID NO: 4 and exhibiting at least a two-fold enhanced ability compared to the ability of the wild type *Thermus aquaticus* polymerase to process nucleic acid in the presence of humic acid at a concentration between 5 and 20%.

3. A kit for amplifying nucleic acid comprising an isolated, engineered polymerase according to claim 1 or claim 2.

* * * * *